(12) United States Patent
Wu et al.

(10) Patent No.: US 7,332,623 B2
(45) Date of Patent: *Feb. 19, 2008

(54) ARYL-SUBSTITUTED ACYCLIC ENEDIYNE COMPOUNDS

(75) Inventors: Ming-Jung Wu, Kaohsiung (TW); Chi-Fong Lin, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 290 days.

This patent is subject to a terminal disclaimer.

(21) Appl. No.: 10/847,667

(22) Filed: May 18, 2004

(65) Prior Publication Data

US 2005/0004212 A1 Jan. 6, 2005

Related U.S. Application Data

(60) Provisional application No. 60/483,887, filed on Jun. 30, 2003.

(51) Int. Cl.
- C07C 255/00 (2006.01)
- C07C 333/16 (2006.01)
- C07C 333/08 (2006.01)
- C07C 49/00 (2006.01)
- C07D 241/02 (2006.01)

(52) U.S. Cl. .................. 558/411; 549/78; 549/80; 544/336; 544/410; 546/339; 546/348; 568/58; 568/328

(58) Field of Classification Search .................. None
See application file for complete search history.

(56) References Cited

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Yoshimatsu et al, "A Novel Synthesis of (Z)-Enynes and (Z)-Enodiynes from Prop-2-ynyl Alcohols" Journal of the Chemical Society, Chemical Communications, pp. 2107-2108 (1994).*
Cao et al, "Direct Conversion of Dipropargylic Sulfones into (E)- and (Z)-Hex-3-ene-1,5-diynes by a Modified One-flask Ramber-Bäcklund Reaction" Tetrahedron Letters, vol. 37(7), pp. 1049-1052 (1996).*
Crousse et al, "Stereoselective Reduction of Conjugated Homopropargylic Alcohols to (E)-Homoallylic Alcohols by Sodium Bis(2-methoxyethoxy) Aluminum Hydride" SYNLETT, vol. 8, pp. 992-994 (1997).*
Uenishi et al, "Stereoselective Hydrogenolysis of 1,1-Dibromo-1-alkenes and Stereospecific Synthesis of Conjugated (Z)-Alkenyl Compounds" Journal of Organic Chemistry, vol. 63, pp. 8965-8975 (1998).*
Wu et al, "A Route to 5-Substituted Dibenzofurans by Anionic Cycloaromatization of 2-(6-substituted-3-hexen-1,5-diynyl)phenyl tert-butyldimethylsilyl ethers and Related Molecules" Angewandte Chemie, vol. 41(21), pp. 4077-4079 (2002).*
James C. Wang, "DNA TOPOISOMERASES", Annu. Rev. Biochem. 1996, 65:635-692.
James C. Wang, "DNA TOPOISOMERASES", Annu. Rev. Biochem. 1985, 54:665-697.
Robert G. Bergman, "Reactive 1,4-Dehydroaromatics[1]", Accounts of Chemical Research, vol. 6, 1973, pp. 25-31.
Kohei Tamao et al., "Optically Active 2,2'-Bis(Diphenylphosphinomethyl)-1,1'-Binaphthyl: A New Chiral Bidentate Phosphine Ligand for Transition-Metal Complex Catalyzed Asymmetric Reactions", Tetrahedron Letters, No. 16, 1977, pp. 1389-1392.
Lawrence F. Povirk et al., "Binding of the Nonprotein Chromophore of Neocarzinostatin to Deoxyribonucleic Acid", Biochemistry, 1980, 19, pp. 4773-4780.
Thomas P. Lockhart et al., "Kinetic Evidence for the Formation of Discrete 1,4-Dehydrobenzene Intermediates. Trapping by Inter- and Intramolecular Hydrogen Atom Transfer and Observation of High-Temperature CIDNP" , J. Am. Chem. Soc. 1981, 103, pp. 4082-4090.

(Continued)

Primary Examiner—Zachary C Tucker
(74) Attorney, Agent, or Firm—Foley & Lardner LLP

(57) ABSTRACT

This invention provides aryl-substituted acyclic enediyne compounds of formula (I):

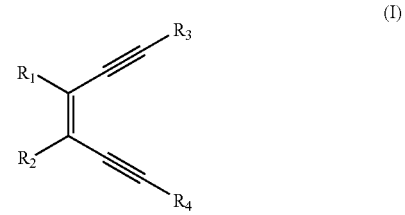

(I)

or a pharmaceutically acceptable salt or solvate thereof, wherein
$R_1=R_2=H$; or $R_1$ and $R_2$ together form a moiety represented by the formula

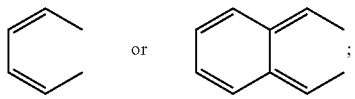

$R_3$ represents a substituted or unsubstituted alkyl having 4-30 carbon atoms, or a substituted or unsubstituted aryl group having 3-30 carbon atoms; and
$R_4$ represents a substituted or unsubstituted aryl group having 3-30 carbon atoms;
with the proviso that $R_3$ is not butyl, pentyl, tetrahydropyranyloxymethyl, tetrahydropyranyloxypropyl or phenyl when $R_1=R_2=H$ and $R_4$ is o-cyanophenyl,; and with the proviso that $R_3$ is not butyl when $R_1=R_2=H$ and $R_4$ is phenyl.

The compounds of formula (I) are found to have inhibitory activities against topoisomerase I or act as a S phase or G2/M phase blocker.

24 Claims, 7 Drawing Sheets

OTHER PUBLICATIONS

Andrew G. Myers, "Proposed Structure of the Neocarzinostatin Chromophore-Methylthioglycolate Adduct; A Mechanism for the Nucleophilic Activation of Neocarzinostatin", Tetrahedron Letters, vol. 28, No. 39, 1987, pp. 4493-4496.

Akira Miyashita et al., "Synthesis of Atropisomeric 2,2'-Bis(dicyclohexylphosphino)-6,6'-dimethyl-1,1'-biphenyl (BICHEP) and It's Use in Rh(I)-catalyzed Asymmetric Hydrogenation of Prochiral Olefins", Chemistry Letters, pp. 1849-1852 (1989).

Andrew G. Myers et al., "Thermal Generation of α,3-Dehydrotoluene from (Z)-1,2,4-Heptatrien-6-yne", J. Am. Chem. Soc. (1989), 111, pp. 8057-8059.

Gerhard Bringmann et al., "The Directed Synthesis of Biaryl Compounds: Modern Concepts and Strategies", Angew. Chem. Int. Ed. Engl. 29, (1990), pp. 977-991.

Suzanne Walker et al., "Sugars as DNA Binders: A Comment on the Calicheamicin Oligosaccharide", J. Am. Chem. Soc. 1990, 112, pp. 6428-6429.

Jacqueline Drak et al., "The carbohydrate domain of calicheamicin γI/1 determines its sequence specificity for DNA cleavage", Proc. Natl. Acad. Sci. USA, vol. 88, pp. 7464-7468, Sep. 1991.

Carlo Rosini et al., "Synthesis and Applications of Binaphthylic $C_2$-Symmetry Derivatives as Chiral Auxiliaries in Enantioselective Reactions", SYNTHESIS, Jun. 1992, pp. 503-517.

Ute Anton et al., "Synthesis of η-Alkyl-Substituted Perylenes and Terrylenes via Alkali-Metal Induced Cyclization of Oligonaphthylenes", Chem. Ber. 1992, 125, pp. 2325-2330.

Hiroshi Sugiyama et al., "A Novel Cyclization Pathway in Activation of Neocarzinostatin Chromophore by Thiol Under Physiological Conditions", Tetrahedron Letters, vol. 33, No. 4, pp. 515-518, 1992.

Simon L. Xu et al., "Sythesis of ρ-Chlorophenols (and -naphthols) from the Thermal Rearrangement of 4-Chlorocyclobutenones", J. Org. Chem. 1992, 57, pp. 326-338.

Philip Magnus et al., "Studies on Dynemicin. A Nonradical Cycloaromatization Pathway for the Azabicyclo[7,3,1] Enediyne Core Structure Initiated by Thiolate Addition", J. Am. Chem. Soc. 1993, 115, pp. 12627-12628.

Stacie J. Froelich-Ammon et al. "Topoisomerase Poisons: Harnessing the Dark Side of Enzyme Mechanism", The Journal of Biological Chemistry, vol. 270, No. 37, Issue of Sep. 15, 1995, pp. 21429-21432.

Malini Gupta et al., "Eukaryotic DNA topoisomerases I", Biochimica et Biophysica Acta 1262 (1995) pp. 1-14.

John R. Lewis "Amaryllidacae alkaloids", Natural Product Reports (NPR), 1995, pp. 303-308.

Shunichi Fukuzumi et al., "Selective two-electron reduction of $C_{60}$ by 10-methyl-9, 10-dihydroacridine via photoinducer electron transfer", Chem. Commun., 1997, pp. 291-292.

Anna Tarli et al., "Synthesis and Thermolysis of Enediynyl Ethyl Ethers as Precursors of Enyne-Ketenes", J. Org. Chem. 1997, 62, pp. 8841-8847.

Wendi M. David et al., "Synthesis and Thermal Rearrangement of C,N-Dialkynyl Imines: A Potential Aza-Bergman Route to 2,5-Didehydropyridine", J. Am. Chem. Soc., 1997, 119, pp. 1464-1465.

Chi-Fong Lin et al., "Cytotoxicities and Topoisomerase I Inhibitory Activities of 2-[2-(2-Alkynylphenyl)ethynyl]benzonitriles, 1-Aryldec-3-ene-1,5-diynes, and Related Bis(enediynyl)arene Compounds", Helvetica Chimica Acta, vol. 85, (2002), pp. 2564-2575.

Ming-Jung Wu et al., "Double Anionic Cycloaromatization of 2-(6-Substituted-3-hexene-1,5-diynyl)-benzonitriles Initiated by Methoxide Addition", Organic Letters, 1999, vol. 1, No. 5, pp. 767-768.

Ming-Jung Wu et al., "Anionic Cycloaromatization of 1-Aryl-3-hexen-1,5-diynes Initiated by Methoxide Addition: Synthesis of Phenanthridinones, Benzo [c]phenanthridinones, and Biaryls", J. Org. Chem. 2002, 67, pp. 5907-5912.

Chi-Fong Lin et al., " A Series of Enediynes as Novel Inhibitors of Topoisomerase I" Bioorganic & Medicinal Chemistry 9 (2001), pp. 1707-1711.

Ming-Jung Wu et al., "Palladium-catalyzed reactions of aryl iodides with trimethylsilylacetylenes and disubstituted alkynes: the synthesis of diarylacetylenes and triarylethylenes", Tetrahedron 57 (2001), pp. 7839-7844.

Chi Fong Lin et al., "Solvent Effects on Aza-anionic Cycloaromatization of 2-(2-Substituted-ethynyl)benzonitriles", Journal of the Chinese Chemical Society, 2001, 48, pp. 211-214.

Wen-Der Lu et al., "Substituent effect on anionic cycloaromatization of 2-(2-substituted ethynyl)benzonitriles and related molecules", Tetrahedron 58 (2002) 7315-7319.

Bertino et al., Chapter 198: Principles of Cancer Therapy in Cecil Textbook of Medicine, 2000, W.B. Saunders Company, pp. 1060-1074.

Gura, "Systems for Identifying New Drugs Are Often Faulty", 11.7/1997, Science, vol. 278, pp. 1041-1042.

\* cited by examiner

ARYL-SUBSTITUTED ACYCLIC ENEDIYNE COMPOUNDS

CROSS-REFERENCE TO RELATED APPLICATION

This application claims the benefits of U.S. Provisional Patent Application Ser. No. 60/483,887, entitled "1,3,4-Trisubstituted-6-aryl-hexen-1,5-diynes, Their Preparation Processes, And Pharmaceutical Compositions Comprising The Same" and filed on Jun. 30, 2003.

BACKGROUND OF THE INVENTION

1. Field of the Invention

This invention relates to aryl-substituted acyclic enediyne compounds, in particular 6-aryl-hexen-1,5-diynes and 1,6-diaryl-hexen-1,5-diynes, which are found to have anti-tumor/cancer cell activities, and the uses of said compounds in the manufacture of pharmaceutical compositions.

2. Description of the Related Art

A series of alkaloids containing enediyne cores which were isolated from *Streptomyces*, have a manifold of biological activities (Walkers, S.; Valentine, K. G.; Kahne, D. *J. Am. Chem. Soc.* 1990, 112, 6428; Dark, L., Iwasawa, N., Danishefsky, S., Crother, D. M., *Proc. Natl. Acad. Sci. USA.* 1991, 88, 7464; Povirk, L. F.; Goldberg, I. H.; *Biochemistry.* 1980, 19, 4773; and Kappen, L. S., Goldberg, I. H., *Nucleic Acid. Res.* 1978, 5, 2959) owing to the generation of radicals. Several biologically active synthetic enediynes are also observed in the formation of radicals. However, besides formation of biradical intermediates, little attentions has been paid to other feasible reaction modes by which enediynes could act and the relative biological activities that enediynes could exhibit, in spite of reports of novel biradical reactions that have begun to surface (Wendi, D. M.; Kerwin, S. M. *J Am. Chem. Soc.* 1997, 119, 1464; Tarli, A., Wang, K. K., *J. Org. Chem.* 1997, 62, 8841; and Xu, S. L., Moore, H. W., *J. Org. Chem.* 1992, 57, 326).

Generation of Radicals from Enediynes

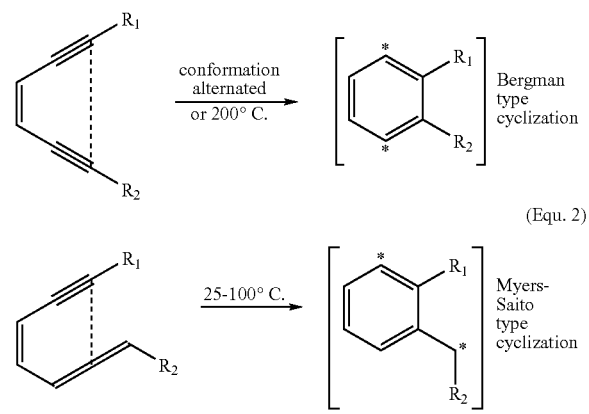

Topoisomerases are important enzymes highly associated with the separation of DNA strands in many cellular metabolic progresses by altering the topological state of duplex DNA. Topoisomerases can be classified into two types based on their mode of cleaving duplex DNA (J. C. Wang, *Annu. Rev. Biochem.* 1996, 65, 635): topo I makes a transient nick on a single-strand of DNA and does not require an energy cofactor (M. Gupta, A. Fujimori, Y. Pommier, *Biochim. Biophys. Acta.* 1995, 1262, 1), whereas topo II acts by nicking both strands of the DNA and hydrolyzes ATP during its catalytic cycle (J. C. Wang, *Annu. Rev. Biochem.* 1985, 54, 665-697; and S. J. Froelich-Ammon, N. Osheroff, *J. Biol. Chem.* 1995, 270, 21429). Topoisomerase I can be isolated from some cellular organisms, including nucleus and mitochondria. Moreover, topo I is present throughout the cell, and its activity varies less than topo II during cell cycle (M. M. Heck, W. N. Hittelman, W. C. Earnshaw, *Proc. Natl. Acad. Sci. USA.* 1988, 85, 1086), which makes topo I inhibitor an attractive target of anticancer, antibacterial, and antiviral drug development.

Although a series of synthetic acyclic enediynes, i.e. 2-(6-substituted-3-hexen-1,5-diynyl)benzonitriles, provided the cytotoxicities on KB and Hep2,2,15 and significant topo I inhibitory properties (C. F. Lin, P. C. Hsieh, W. D. Lu, H. F. Chiu, M. J. Wu, *J. Bioorg. Med. Chem.* 2001, 9, 1707) in low micro-molar concentration ranges (see the following Scheme 1), the precision relationships between the cytotoxicities and these unique structures were still under investigation. This prompted us to further investigate the structure-activity-relationships (SAR) of new enediyne compounds.

Scheme 1

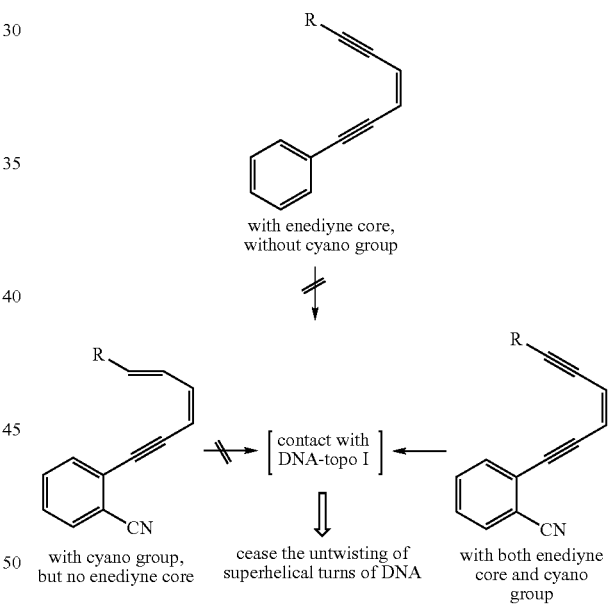

On the other hand, in our earlier research work, we reported that treatment of 2-(6-substituted-3-hexen-1,5-diynyl)benzonitriles with sodium methoxide in methanol at reflux gives phenanthridinones and substituted biphenyl derivatives (M.-J. Wu et al. (1999), *Org. Lett.,* 1, 767). Although the chemical yields are low, this reaction constitutes a novel cycloaromatization of enediynes (for examples, for nonradical cycloaromatization of enediynes, reference may be made to P. Magnus et al. (1993), *J. Am. Chem. Soc.,* 115, 12627 and H. Sugiyama et al. (1992), *Tetrahedron Lett.* 1992, 33, 515) and a new synthetic approach to phenanthridinones and biphenyls.

Since phenanthridinones (Lewis, J. R. (1997), *Nat. Prod. Rep.,* 14, 303), biphenyls (Bringmann, G.; Water, R.; Weirich, R. *Angew. Chem., Int. Ed. Engl.* 1990, 29, 977; Acton, U.; Goltner, C.; Mullen, K. *Chem. Ber.* 1992, 125, 2325; Rosin, C.; Franzin, L.; Rafaeli, A.; Salvadori, P. *Synthesis* 1992, 6, 503; Tamao, K.; Yamamoto, H.; Matsumoto, H.; Miyake, N.; Hayashi, Y.; Kumada, M. *Tetrahedron Lett.* 1977, 47, 1389; and Miyashita, A.; Karino, H.; Shimamura, J. I.; Chiba, T.; Nagano, K.; Nohira, H.; Takaya, H. *Chem. Lett.* 1989, 1849), and structurally related compounds are of current interest in the pharmaceutical area and for the preparation of new materials, methods for the selective preparation of these compounds have considerable value.

A proposed mechanism for the formation of phenanthridinones is methoxide addition to the cyano group, followed by an anionic cascade cycloaromatization. In contrast, methoxide addition to C2 of the acetylenic moiety and the same type of cycloaromatization will give biphenyls (see the following Scheme 2).

Scheme 2

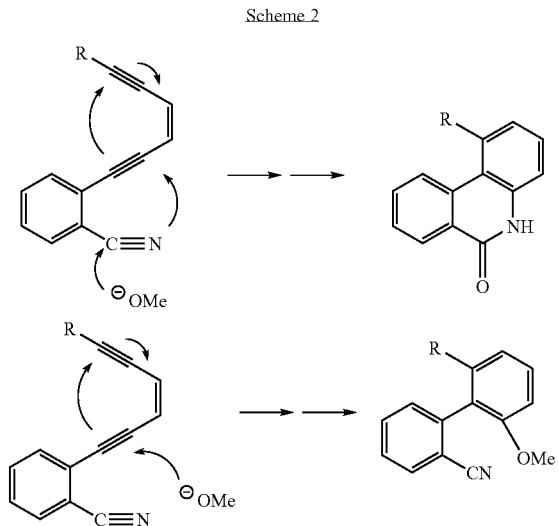

We believe that the low yields in these reactions are due to poor regioselectivity in the nucleophilic addition of methoxide to the conjugated system. Thus, we anticipated that introducing a polar aprotic solvent into the reaction mixture would increase the nucleophilicity and the hardness of the nucleophile and therefore promote regioselectivity in the nucleophilic addition step to increase the chemical yield.

SUMMARY OF THE INVENTION

Accordingly, the present invention provides a compound of formula (I) or a pharmaceutically acceptable salt or solvate thereof:

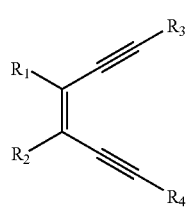

(I)

wherein
$R_1=R_2$ H; or $R_1$ and $R_2$ together form a moiety represented by the formula

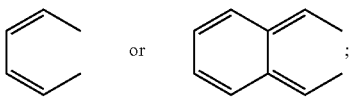

$R_3$ represents a substituted or unsubstituted alkyl having 4-30 carbon atoms, or a substituted or unsubstituted aryl group having 3-30 carbon atoms; and
$R_4$ represents a substituted or unsubstituted aryl group having 3-30 carbon atoms;
with the proviso that $R_3$ is not butyl, pentyl, tetrahydropyranyloxymethyl, tetrahydropyranyloxypropyl or phenyl when $R_1=R_2=H$ and $R_4$ is o-cyanophenyl,; and with the proviso that $R_3$ is not butyl when $R_1=R_2=H$ and $R_4$ is phenyl.

The above-described compounds of formulas (I) are found to have cytotoxicity against tumor/cancer cells, such as leukemia cancer cells, non-small-cell lung cancer cells, colon cancer cells, CNS cancer cells, melanoma cancer cells, ovarian cancer cells, renal cancer cells, prostate cancer cells and breast cancer cells, in particular human oral epidermoid carcinoma cell, human cevix epitheloid carcinoma cell, human colon adenocarcinoma cell, human lung large cell carcinoma cell, and human hepatoma cell. Therefore, the present invention also anticipates the uses of the above-described compounds of formulas (I), in its free form or a pharmaceutically acceptable salt or solvate thereof, in the manufacture of pharmaceutical compositions for inhibiting the growth of tumor/cancer cells, including leukemia cancer cells, non-small-cell lung cancer cells, colon cancer cells, CNS cancer cells, melanoma cancer cells, ovarian cancer cells, renal cancer cells, prostate cancer cells and breast cancer cells.

BRIEF DESCRIPTION OF THE DRAWINGS

The above and other features and advantages of the present invention will become apparent in the following detailed description of the preferred embodiments with reference to the accompanying drawing, of which.

DETAILED DESCRIPTION OF THE INVENTION

Figure 1:
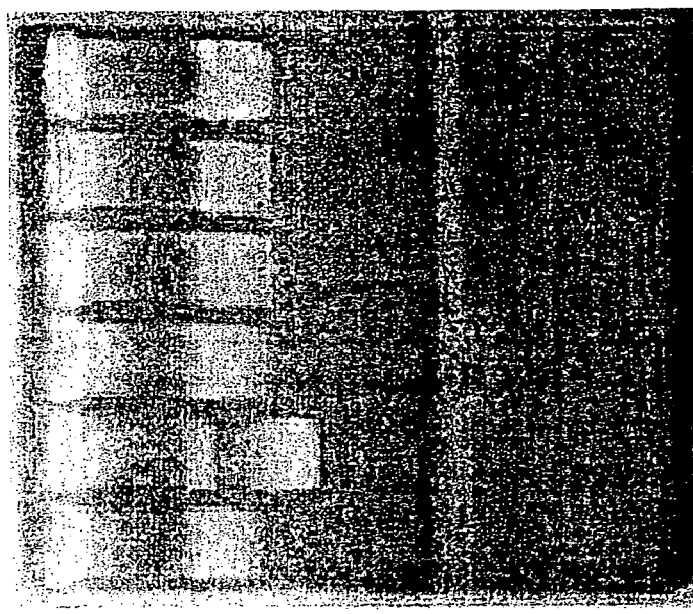
FIG. 1 shows the cleavage of supercoiled pGEM9zf(-) DNA by topoisomerase I in the presence of 2-[2-(2-alkynylphenyl)ethynyl]benzonitriles 7-10, 1,4-bis(dec-3-ene-1,5-diynyl)benzene 11, and 4,4'-bis(dec-3-ene-1,5-diynyl)-1,1'-biphenyl 12, in which in panel (a), lane 1: DNA+topo I; lane 2: DNA only; lane 3: DNA+topo I+camptothecin (43.5 µM); lanes 4-6: DNA+topo I+compound 10, lanes 7-9: DNA+topo I+compound 9; and in panel (b), lane 1: DNA+topo I; lane 2: DNA only; lanes 3-4: DNA+topo I+compound 11; and lanes 5-6: DNA+topo I+compound 12.
Figure 1:
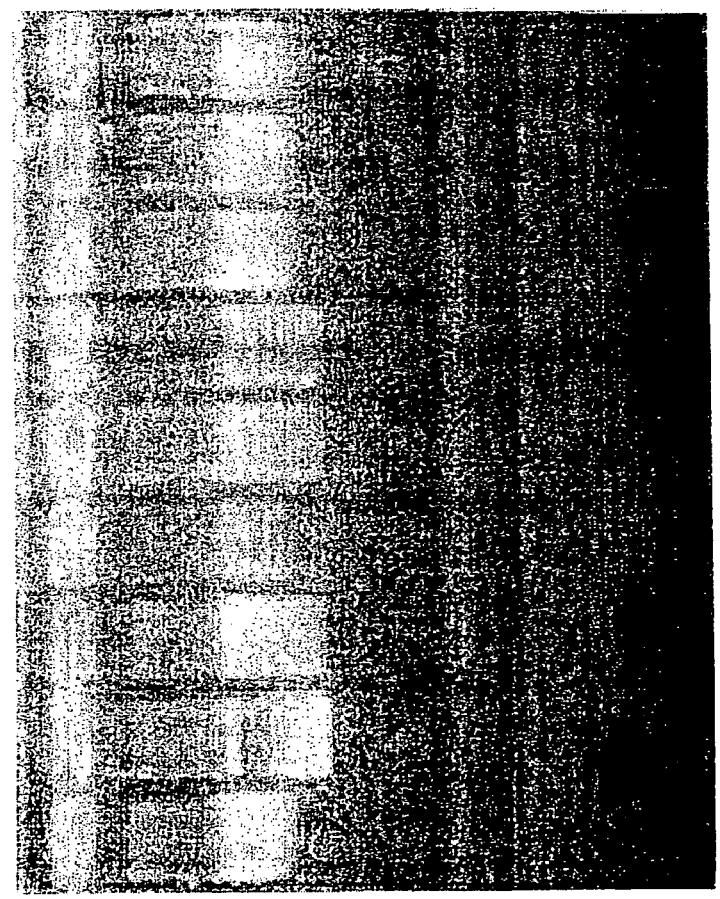

In our earlier research work (C. F. Lin et al. (2001), *J. Bioorg. Med. Chem.*, 9, 1707-1711), we screened a series of 2-(6-substituted-3(Z)-hexen-1,5-diynyl)benzonitriles which showed potent cytotoxicity with KB cell (see the following Table 1). The high cytotoxicity of these 2-(6-substituted-3(Z)-hexen-1,5-diynyl) benzonitriles promoted our further studies toward this unexpected biological behavior.

TABLE 1

Cytotoxicities of
2-(6-substituted-3(Z)-hexen-1,5-diynyl)benzonitriles
($IC_{50}$)

1. R = $CH_2OTHP$
2. R = $(CH_2)_3OTHP$
3. R = $(CH_2)_3CH_3$
4. R = $(CH_2)_4CH_3$ (THP means 3,4,5,6-tetrahydro-2H-pyran-2-yl)

| Cpd\Cell | KB | Hep2,2,15 |
|---|---|---|
| 1 | 0.1 μM | >10 μM |
| 2 | <$10^{-2}$ μM | >10 μM |
| 3 | <$10^{-2}$ μM | 17 μM |
| 4 | <$10^{-2}$ μM | >10 μM |

It is considered that these molecules comprise an enediyne structure, but unlike the accustomed mode of enediynes (Jones, R. R., Bergman, R. G., *J. Am. Chem. Soc.* 1972, 94, 660; Bergman, R. G., *Acc. Chem. Res.* 1973, 6, 25; Lockhart, T. P., Comita, P. B., Bergman, R. G., *J. Am. Chem. Soc.* 1981, 103, 4082; Myers, A. G., Kuo, E. Y, Finny, N. S., *J. Am. Chem. Soc.* 1989, 111, 8057; and Myers, A. G., *Tetrahedron Lett.* 1987, 28, 4493) which generate biradicals and facilitate the decease of cells (scheme A), there is no initiating factor to promote the enediynes to form active biradicals via Myers cycloaromatization (path a). Similarly, according to Bergman's reports, the acyclic enediynes cannot cycloaromatize to produce biradical intermediates under 37° C. (path b).

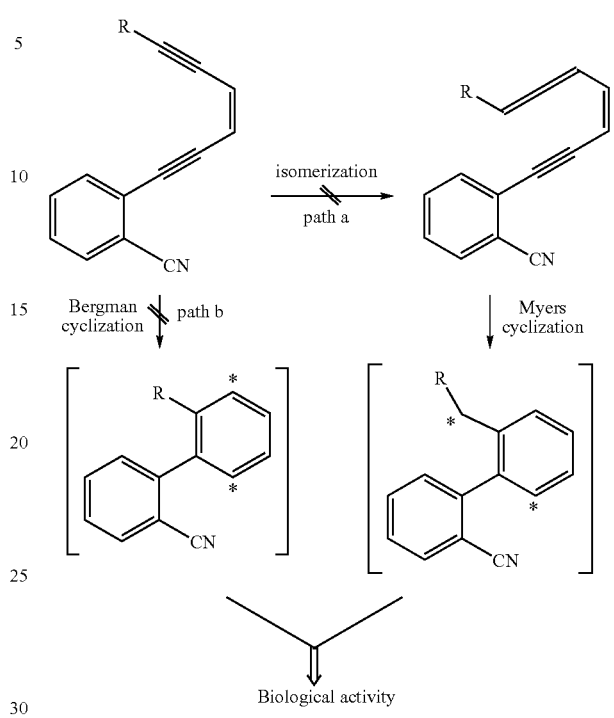

Scheme A

From an overview of the possible mechanisms which anticancer drugs would proceed, the most probable pathway of 2-(6-substituted-3(Z)-hexen-1,5-diynyl)benzonitriles to induce the death of cancer cells is the physiological enzyme inhibitors, especially the topological enzymes, i.e. the topoisomerase, which are essential for DNA replication, transcription, repair, recombination, and chromosome segregation (Champoux, J. J. in DNA Topology and its Biological Effects, Wang, J. C. and Cozzarelli, N. R. Eds. (Cold Spring Harbor Labortory, Cold Spring Harbor, N.Y, 1990). pp217-242; and Wang, J. C., *Annu. Rev. Biochem.* 1996, 65, 635). Exploration of the requisite fundamental mainstay of these compounds and the precision relationships between the cytotoxicities and these unique structures are still under investigation.

To further investigate the biological activities of 2-(6-substituted-3(Z)-hexen-1,5-diynyl)benzonitriles, new aryl-substituted acyclic enediyne compounds, in particular 6-aryl-hexen-1,5-diynes and 1,6-diaryl-hexen-1,5-diynes, were designed and synthesized by modification of the enediyne core and the aryl group(s) bearing on it, and their cytotoxicities were evaluated in terms of cytotoxic activities against human solid tumor cells, the topoisomerase I inhibitory activities and the cell cycle analysis.

Therefore, this invention provides a compound of formula (I) or a pharmaceutically acceptable salt or solvate thereof:

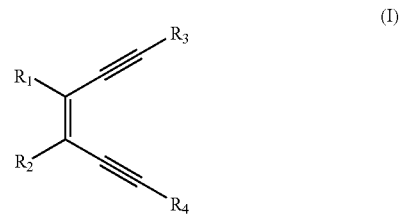

(I)

wherein $R_1=R_2=H$; or $R_1$ and $R_2$ together form a moiety represented by the formula

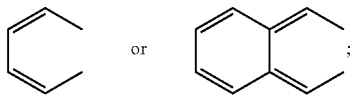

$R_1=R_2=H$; or $R_1$ and $R_2$ together form a moiety represented by the formula

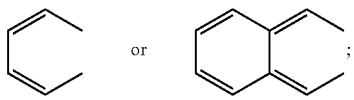

$R_3$ represents a substituted or unsubstituted alkyl having 4-30 carbon atoms, or a substituted or unsubstituted aryl group having 3-30 carbon atoms; and $R_4$ represents a substituted or unsubstituted aryl group having 3-30 carbon atoms;

with the proviso that $R_3$ is not butyl, pentyl, tetrahydropyranyloxymethyl, tetrahydropyranyloxypropyl or phenyl when $R_1=R_2=H$ and $R_4$ is o-cyanophenyl,; and with the proviso that $R_3$ is not butyl when $R_1=R_2=H$ and $R_4$ is phenyl.

In a preferred embodiment of this invention, both $R_1$ and $R_2$ are H.

In another preferred embodiment of this invention, $R_1$ and $R_2$ together form a moiety represented by the formula

Preferably, $R_3$ represents a substituted or unsubstituted alkyl having 4-20 carbon atoms, and more preferably 4-10 carbon atoms, or an aryl group having 3-20 carbon atoms, and more preferably 3-10 carbon atoms.

In a preferred embodiment of this invention, $R_3$ represents: butyl, t-butyl, pentyl, hexyl, heptyl or octyl, each of which is optionally substituted with one to three substituents selected from the group consisting of halo, cyano, amino, nitro, carbonyl, carboxyl, hydroxy, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, and $C_1$-$C_6$ alkanoyloxy; thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is optionally substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl; ($C_5$-$C_8$ aryl)oxyalkyl, such as tetrahydropyranyloxyalkyl; or a phenyl group which is unsubstituted or substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

In a more preferred embodiment of this invention, $R_3$ represents: butyl, t-butyl, pentyl, tetrahydropyranyloxyalkyl, 2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, 1-(4-phenyl)pyrrolidinyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl or 2-thioanisyl.

In a further preferred embodiment of this invention, $R_3$ is an aryl group selected from o-cyanophenyl, m-cyanophenyl, p-cyanophenyl, p-trifluoromethylphenyl, m-trifluoromethylphenyl, o-trifluoromethylphenyl,

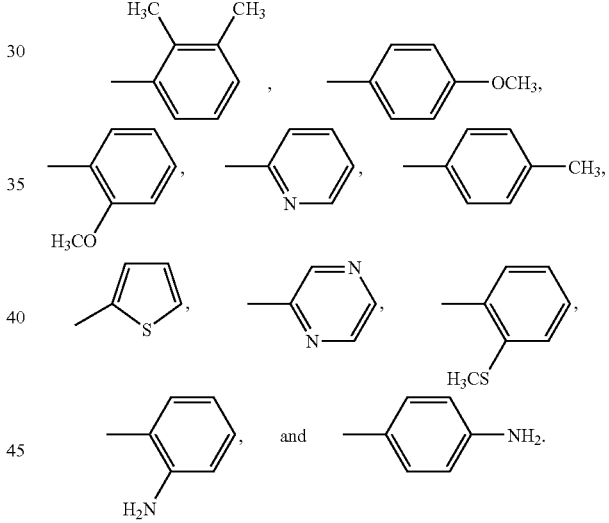

Preferably, $R_4$ represents a substituted or unsubstituted aryl group having 3-20 carbon atoms, and more preferably 3-10 carbon atoms.

In a preferred embodiment of this invention, $R_4$ represents: thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is optionally substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl; ($C_5$-$C_8$ aryl)oxyalkyl, such as tetrahydropyranyloxyalkyl; or a phenyl group which is unsubstituted or substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy; or a group represented by the formula

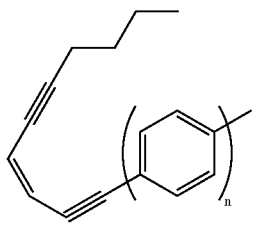

where n=1 or 2.

In a more preferred embodiment of this invention, $R_4$ represents: tetrahydropyranyloxyalkyl, 2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, 1-(4-phenyl)pyrrolidinyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl, 2-thioanisyl, or a group represented by the formula

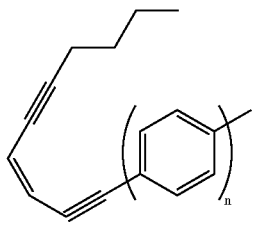

where n=1 or 2.

In a further preferred embodiment of this invention, $R_4$ is an aryl group selected from: o-cyanophenyl, m-cyanophenyl, p-cyanophenyl, p-trifluoromethylphenyl, m-trifluoromethylphenyl, o-trifluoromethylphenyl,

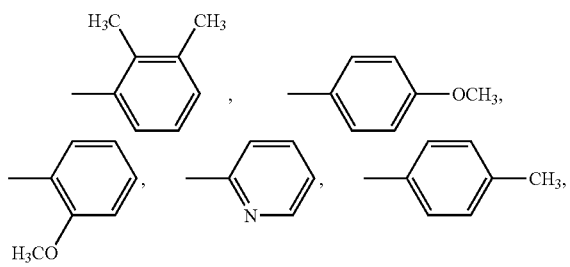

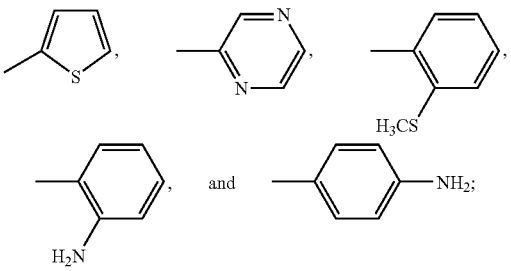

represented by the formula

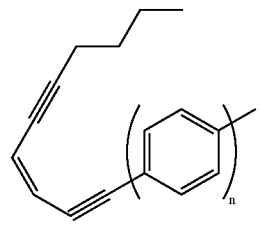

where n=1 or 2.

In a preferred embodiment of this invention, the compound of formula (I) or a pharmaceutically acceptable salt or solvate thereof is one having the following formula (IA):

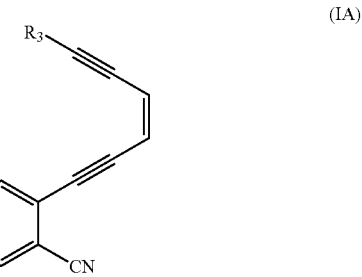

(IA)

wherein $R_3$ represents: a tetrahydropyranyloxyalkyl group excluding tetrahydropyranyloxymethyl and tetrahydropyranyloxypropyl; thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is optionally substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl; or a phenyl group which is unsubstituted or substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

In a further preferred embodiment of this invention, the compound of formula (IA) is one where $R_3$ is an aryl group selected from 2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, 1-(4-phenyl)pyrrolidinyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl, and 2-thioanisyl.

In a further preferred embodiment of this invention, the compound of formula (IA) is one where $R_3$ is an aryl group selected from o-cyanophenyl, m-cyanophenyl, p-cyanophenyl, p-trifluoromethylphenyl, m-trifluoromethylphenyl, o-trifluoromethylphenyl,

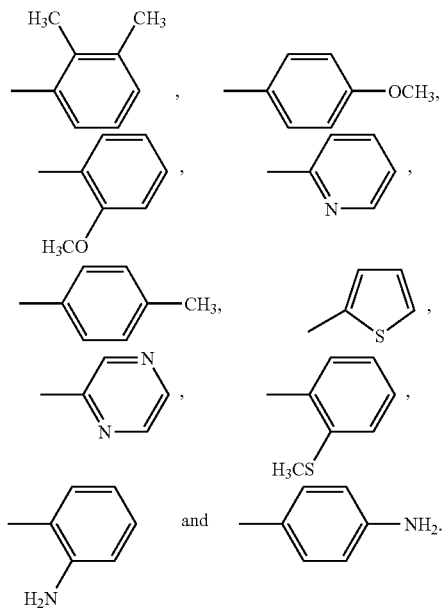

In a preferred embodiment of this invention, the compound of formula (I) or a pharmaceutically acceptable salt or solvate thereof is one having the following formula (IB):

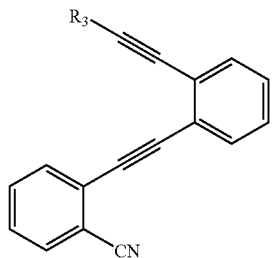

(IB)

wherein $R_3$ represents: butyl, t-butyl, pentyl, hexyl, heptyl or octyl, each of which is optionally substituted with one to three substituents selected from the group consisting of halo, cyano, amino, nitro, carbonyl, carboxyl, hydroxy, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, and $C_1$-$C_6$ alkanoyloxy; thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is optionally substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl; ($C_5$-$C_8$ aryl)oxyalkyl, such as tetrahydropyranyloxyalkyl; or a phenyl group which is unsubstituted or substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

In a more preferred embodiment of this invention, the compound of formula (IB) is one where $R_3$ represents: butyl, t-butyl, pentyl, tetrahydropyranyloxyalkyl, 2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, 1-(4-phenyl)pyrrolidinyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl or 2-thioanisyl.

In a further preferred embodiment of this invention, the compound of formula (IB) is one where $R_3$ is butyl, pentyl, tetrahydropyranyloxymethyl or tetrahydropyranyloxypropyl, or an aryl group selected from o-cyanophenyl, m-cyanophenyl, p-cyanophenyl, p-trifluoromethylphenyl, m-trifluoromethylphenyl, o-trifluoromethylphenyl,

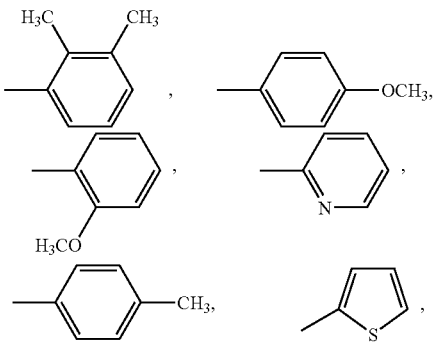

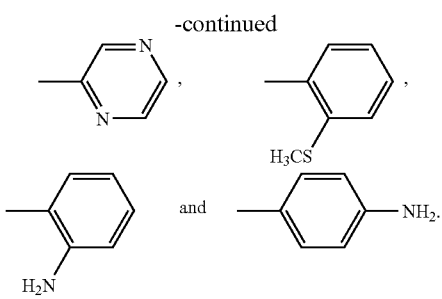

In a preferred embodiment of this invention, the compound of formula (I) or a pharmaceutically acceptable salt or solvate thereof is one having the following formula (IC):

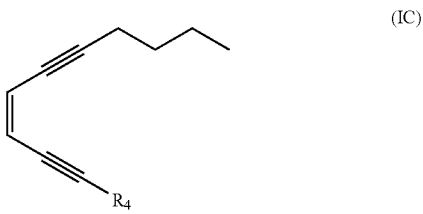

(IC)

wherein $R_4$ represents: thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is optionally substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl; ($C_5$-$C_8$ aryl)oxyalkyl, such as tetrahydropyranyloxyalkyl; or a phenyl group which is unsubstituted or substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy; or a group represented by the formula

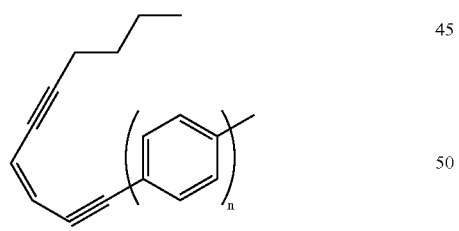

where n=1 or 2.

In a more preferred embodiment of this invention, the compound of formula (IC) is one where $R_4$ represents: tetrahydropyranyloxyalkyl, 2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, 1-(4-phenyl)pyrrolidinyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl, 2-thioanisyl, or a group represented by the formula

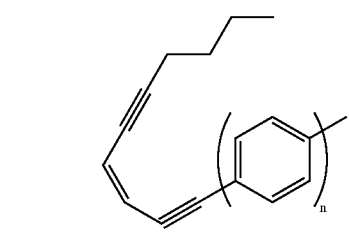

where n=1 or 2.

In a further more preferred embodiment of this invention, the compound of formula (IC) is one where $R_4$ is an aryl group selected from: o-cyanophenyl, m-cyanophenyl, p-cyanophenyl, p-trifluoromethylphenyl, m-trifluoromethylphenyl, o-trifluoromethylphenyl,

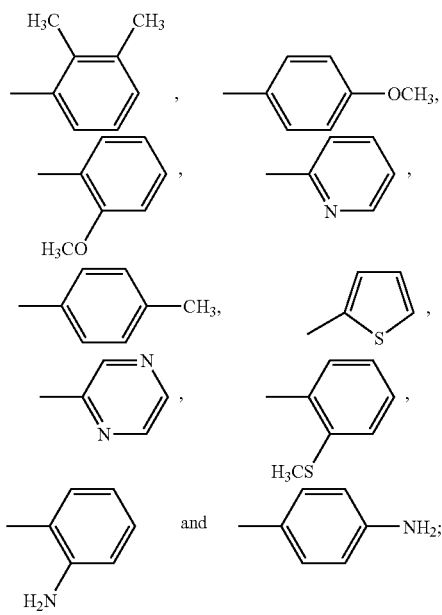

or a group represented by the formula

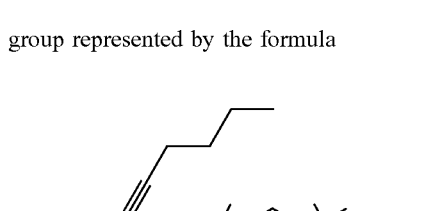

where n=1 or 2.

In another preferred embodiment of this invention, the compound of formula (I) or a pharmaceutically acceptable salt or solvate thereof is one having the following formula (ID):

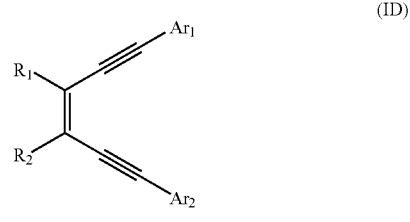

wherein
R₁=R₂=H; or R₁ and R₂ together form a moiety represented by the formula of

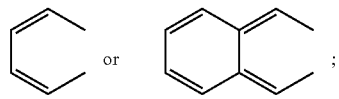

and
Ar₁ and Ar₂ independently represent an aryl group selected from thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is optionally substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl; ($C_5$-$C_8$ aryl)oxyalkyl, such as tetrahydropyranyloxyalkyl; or a phenyl group which is unsubstituted or substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

In a more preferred embodiment of this invention, the compound of formula (ID) is one where Ar₁ and Ar₂ independently represent: tetrahydropyranyloxyalkyl, 2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, 1-(4-phenyl)pyrrolidinyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl or 2-thioanisyl.

In a more preferred embodiment of this invention, the compound of formula (ID) is one where Ar₁ and Ar₂ independently represent an aryl group selected from o-cyanophenyl, m-cyanophenyl, p-cyanophenyl, p-trifluoromethylphenyl, m-trifluoromethylphenyl, o-trifluoromethylphenyl,

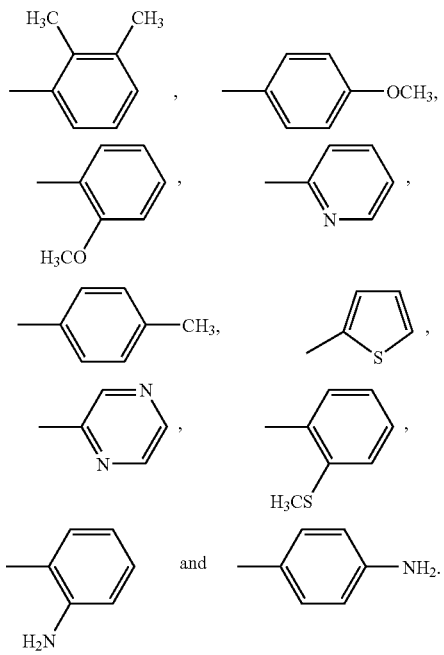

In a most preferred embodiment of this invention, the compound of formula (ID) is one where Ar₁ and Ar₂ are identical and represent an aryl group selected from o-cyanophenyl, m-cyanophenyl, p-cyanophenyl, p-trifluoromethylphenyl, m-trifluoromethylphenyl, o-trifluoromethylphenyl,

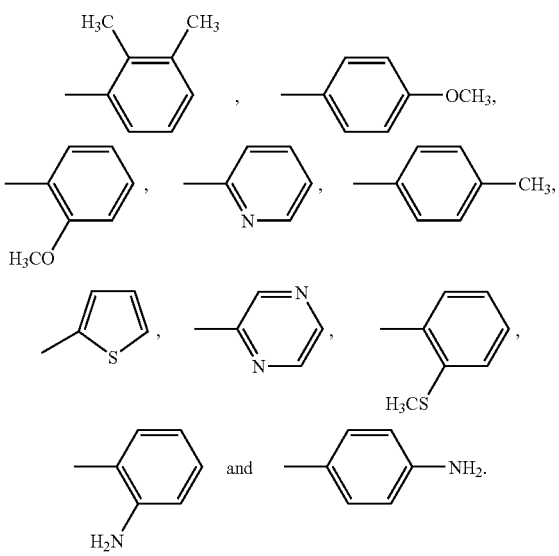

In a still further preferred embodiment of this invention, the compound of formula (I) is

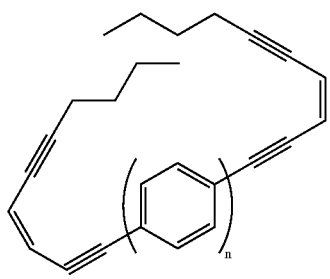

where n is 1 or 2.

According to this invention, the compounds of formula (I) may be in their free form or in the form of a pharmaceutically acceptable salt or solvate thereof.

Illustrative pharmaceutically acceptable salts include metal salts such as sodium salt, potassium salt, calcium salt, magnesium salt, manganese salt, iron salt and aluminum salt; mineral acid addition salts such as hydrochloride, hydrobromide, hydroiodide, sulfate and phosphate; organic acid addition salts such as benzoate, methanesulfonate, ethanesulfonate, benzenesulfonate, p-toluenesulfonate, oxalate, maleate, fumarate, tartrate and citrate; and those with amino acids, such as arginine, aspartic acid and glutamic acid.

In addition, the compound of formula (I) of the present invention may also exist as a stereoisomer or in the form of solvates represented by the hydrate. Therefore, it is contemplated that these stereoisomers and solvates fall within the technical concept of the present invention.

This invention also provides a convenient and efficient process for producing a compound of formula (I) or a pharmaceutically acceptable salt or solvate thereof,

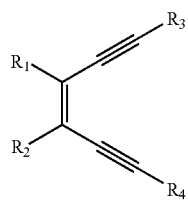
(I)

wherein $R_1=R_2=H$; or $R_1$ and $R_2$ together form a moiety represented by the formula of

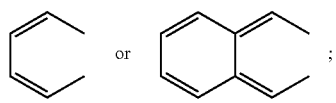

$R_3$ represents a substituted or unsubstituted alkyl having 4-30 carbon atoms, or a substituted or unsubstituted aryl group having 3-30 carbon atoms; and $R_4$ represents a substituted or unsubstituted aryl group having 3-30 carbon atoms;

the process comprising the steps of:

(i) forming a compound of formula (II) by reacting a compound of formula (IIA) with a compound of formula (III) in ethyl ether in the presence of $Pd(PPh_3)_4$, CuI and $n$-$BuNH_2$,

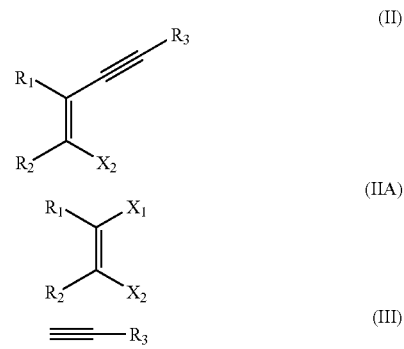

wherein $R_1$, $R_2$ and $R_3$ respectively correspond to those defined for formula (I);

$X_1$ and $X_2$ independently represent a halogen atom;

(ii) forming a compound of formula (IIB) by treating the resultant compound of formula (II) from step (i) with trimethylsilylacetylene in ethyl ether in the presence of $Pd(PPh_3)_4$, CuI and $n$-$BuNH_2$, followed by a desilylation treatment with tetrabutylammoniumfluoride,

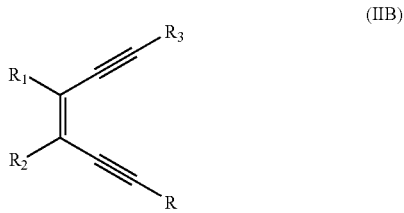

wherein $R_1$, $R_2$ and $R_3$ respectively correspond to those defined for formula (I), and R is H; and (iii) reacting the resultant compound of formula (IIB) from step (ii) with a compound of $R_4I$, where $R_4$ corresponds to that defined for formula (I), in ethyl ether in the presence of $Pd(PPh_3)_4$, CuI and $n$-$BuNH_2$.

According to this invention, acyclic enediyne compounds 1-43 of formula (I) having structures shown below can be produced from the process of this invention using a corresponding 1,2-disubstituted-dihaloethene compound A1 of formula (IIA) as a starting material based on the following synthesis scheme 3. Coupling reaction (K. Sonogashira et al. (1997), *Chem. Comm.*, 291) of the compound A1 with 2-substitutedacetylene ($R_3$=alkyl, aryl) using palladium as a catalyst in an ether solution at 25° C. for 4 hours gave compound A2. Likewise, compound A2 was coupled with trimethylsilylacetylene to give compound A3. Treatment of compound A3 with TBAF in THF solution produced the desilylated compound A4. Finally, acyclic enediyne compounds 1-43 are produced from palladium-catalyzed coupling reaction of corresponding compounds A4 with various aryl iodides.

Scheme 3

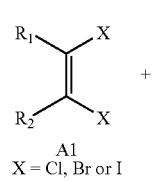
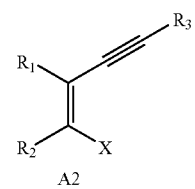
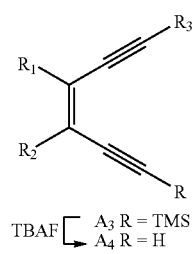

Structures of Acyclic Enediyne Compounds 1-23

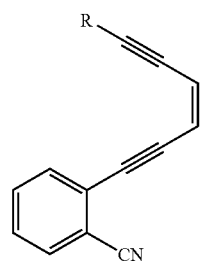

1. R = CH$_2$OTHP
2. R = (CH$_2$)$_3$OTHP
3. R = (CH$_2$)$_3$CH$_3$
4. R = (CH$_2$)$_4$CH$_3$
5. R = C$_6$H$_5$

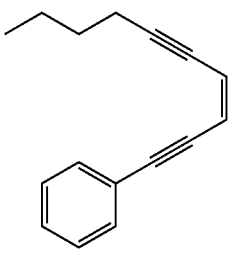

6

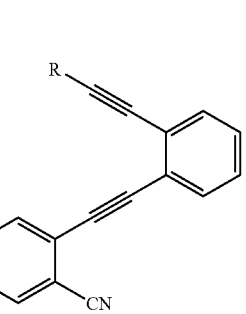

7. R = (CH$_2$)OTHP
8. R = (CH$_2$)$_3$OTHP
9. R = (CH$_2$)$_3$CH$_3$
10. R = (CH$_2$)$_4$CH$_3$

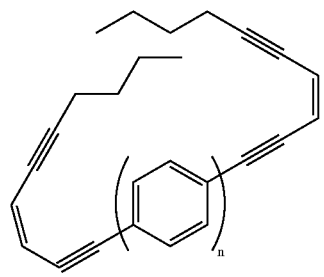

11. n = 1
12. n = 2

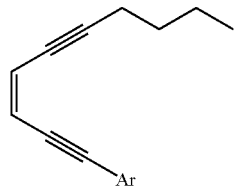

13. Ar = p-ClC$_6$H$_4$
14. Ar = p-CNC$_6$H$_4$
15. Ar = pyridinyl
16. Ar = thienyl
17. Ar = pyrazinyl
18. Ar = p-CF$_3$C$_6$H$_4$
19. Ar = m-CF$_3$C$_6$H$_4$
20. Ar = o-CF$_3$C$_6$H$_4$
21. Ar = p-NO$_2$C$_6$H$_4$
22. Ar = o-CH$_3$CO$_2$C$_6$H$_4$
23. Ar = p-CH$_3$COC$_6$H$_4$ Structures of Acyclic Enediyne Compounds 24-33

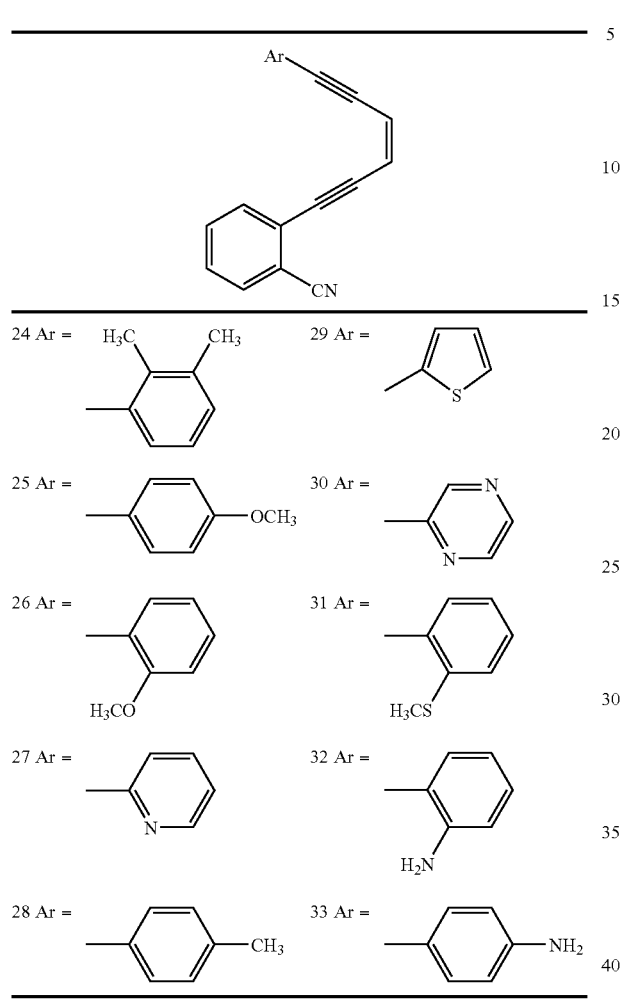

Structures of Acyclic Enediyne Compounds 34-43

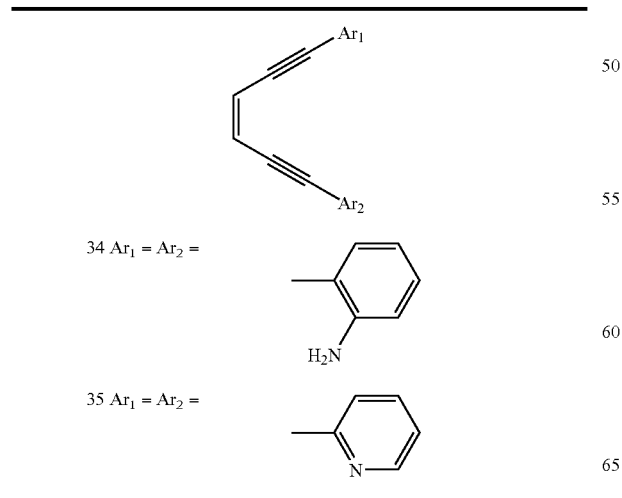

36 Ar$_1$ = Ar$_2$ = 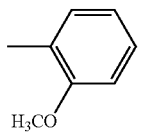

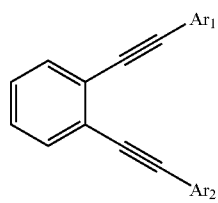

37 Ar$_1$ = Ar$_2$ = 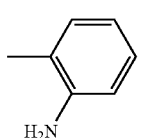

38 Ar$_1$ = Ar$_2$ = 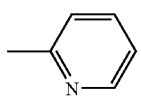

39 Ar$_1$ = Ar$_2$ = 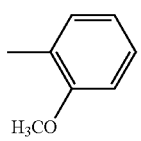

40 Ar$_1$ = Ar$_2$ = 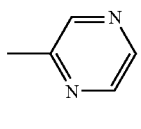

41 Ar$_1$ = Ar$_2$ = 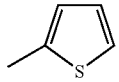

42 Ar$_1$ = Ar$_2$ = p-CF$_3$C$_6$H$_4$

43 Ar$_1$ = Ar$_2$ = 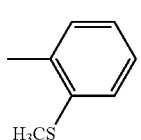

Alternatively, compounds of formula (IB), such as compounds 24-33 listed above, may be produced according to the following synthesis scheme 4, in which the percent yield of each compound is parenthesized.

Scheme 4

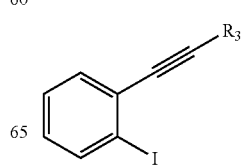

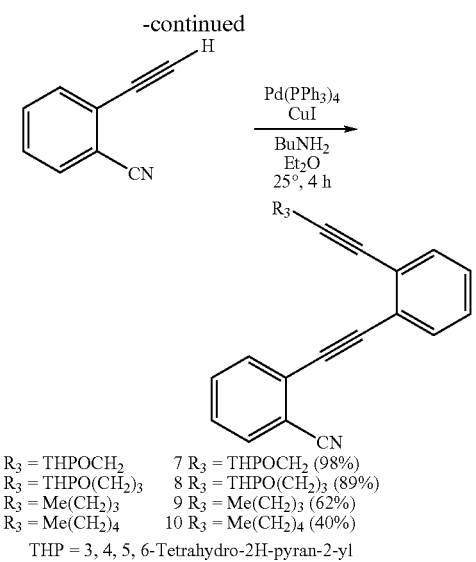

R₃ = THPOCH₂     7 R₃ = THPOCH₂ (98%)
R₃ = THPO(CH₂)₃  8 R₃ = THPO(CH₂)₃ (89%)
R₃ = Me(CH₂)₃    9 R₃ = Me(CH₂)₃ (62%)
R₃ = Me(CH₂)₄   10 R₃ = Me(CH₂)₄ (40%)
THP = 3, 4, 5, 6-Tetrahydro-2H-pyran-2-yl Alternatively, compounds of formula (ID) of this invention, such as compounds 34-43 listed above, may be produced from the coupling reaction of 1,2-disubstituted-dihaloethene with a selected 2-aryl-1-ethyne according to the following synthesis scheme 5:

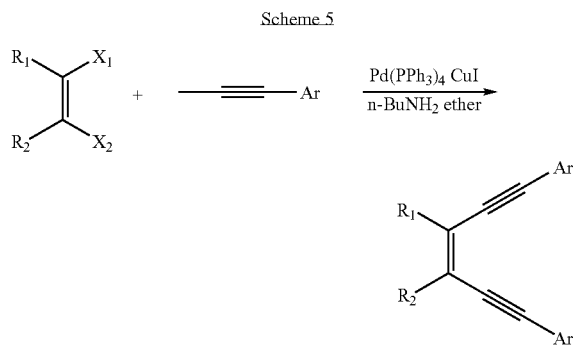

Scheme 5

The compounds of formula (I) according to this invention have been demonstrated to exhibit inhibitory activities against the growth of several solid tumor cell lines, in particular human oral epidermoid carcinoma cell, human cervix epitheloid carcinoma cell, human colon adenocarcinoma cell, human lung large cell carcinoma cell, and human hepatoma cell. Further in vitro tests show that the compounds of formula (I) may inhibit the activity of topoisomerase I or block the S phase or G2/M phase of tumor cells' cell cycle. Therefore, the present invention also envisions the application of the compounds of formula (I) of this invention in the manufacture of pharmaceutical compositions.

Optionally, the pharmaceutical composition according to this invention may additionally comprise a pharmaceutically acceptable carrier widely employed in the art for the manufacture of medicaments. For example, the pharmaceutically acceptable carrier can include one or more than one of the following reagents: solvents, disintegrating agents, binders, excipients, lubricants, absorption delaying agents and the like.

The pharmaceutical composition according to this invention may be administered parenterally or orally in a suitable pharmaceutical form. Suitable pharmaceutical forms include sterile aqueous solutions or dispersions, sterile powders, tablets, troches, pills, capsules, and the like.

In addition, the active compounds of the present invention may be incorporated into sustained-release preparations and formulations. Optionally, the pharmaceutical composition according to this invention may be administered alone or in conjunction with an additional anticancer agent, such as such as Mitomycin, Adriamycin, Actinomycin, cis-platin and the like.

In addition, the compounds of formula (I) may be used in the synthesis of phenanthridinones, benzo[c]phenanthridinones and biaryls, which in turn may be developed into useful pharmaceuticals, by anionic cycloaromatization of said compounds with sodium methoxide in refluxing methanol in the presence of a polar aprotic solvent, such as DMSO, HMPA, THF, or 18-crown-6, according to schemes described in M. J. Wu et al. (2002), *J. Org. Chem.*, 67, 5907-5912, the whole disclosure of which is incorporated herein by reference.

The present invention will be described in more detail with reference to the following examples, which are given solely for the purpose of illustration and are not intended to limit the scope of the present invention.

EXAMPLES

I. General Synthesis Procedures

Method A:

To a degassed solution of (trimethylsilyl)acetylene (12 mmole) in Et₂O (25 mL) containing CuI (3.2 mmole) and n-BuNH₂ (34 mmole) in Et₂O (25 ML) was added a degassed solution of cis-1,2-dichloroethylene or 1,2-diiodobenzene (12 mmole) containing Pd(PPh₃)₄ (0.8 mmole) in Et₂O (25 mL). The resulting reaction mixture was stirred for 6 hrs, and quenched with saturated aqueous NH₄Cl solution. The aqueous layer was extracted with EtOAc (50 mL), and the combined organic extracts were washed with saturated aqueous Na₂CO₃ solution (40 mL) and dried over anhydrous MgSO₄. After filtration and removal of solvent in vacuo, the residue was purified by column chromatography on silica gel (hexanes as eluent) to give the desired products.

Method B:

To a stirred solution of 2-(2-trimethylsilyl-1-ethynyl)iodobenzene (5.6 mmol) in dry DMF (40 mL) was added Pd(PPh₃)₄ (0.22 mmol), followed by Zn(CN)₂ (1.25 mmol). The resulting reaction mixture was degassed, heated to reflux and stirred for 5 hrs. After cooling to room temperature, the reaction mixture was quenched with 2 N aqueous NH₄OH and extracted with EtOAc. The combined organic extracts were washed with brine and dried over anhydrous MgSO₄.

Method C:

After filtration and removal of solvent, K₂CO₃ (5 eq) was then added to a stirred solution of 2-(2-trimethylsilyl-1-ethynyl)benzonitrile in dry MeOH (20 mL). The resulting reaction mixture was degassed and stirred for 2 hrs at room temperature. After filtration and removal of solvent, the reaction mixture was quenched with saturated aqueous NaHCO₃ solution. The aqueous layer was extracted with EtOAc. The combined organic extracts were washed with brine, and dried over anhydrous MgSO₄. After filtration and removal of solvent, the residue was purified by column chromatography on silica gel (eluent=hexane/EA, 15:1) to give the desired products.

II. General Procedures of the Coupling Reaction of 1,2-disubstituted-dihaloethene with 2-substituted-1-ethene A degassed solution of 1,2-disubstituted-dihaloethene (12 mmol) in dry ether (30 mL) containing Pd(PPh$_3$)$_4$ (0.8 mmol) and CuI (3.2 mmol) was added to a solution of 2-substituted-1-ethene (24 mmol) containing n-butylamine (34 mmol). The resulting solution was stirred at 25° C. for 6 hrs, quenched with saturated aqueous NH$_4$Cl and Na$_2$CO$_3$ solutions, and extracted with EtOAc. The organic layer was separated and dried over MgSO$_4$. After filtration, the solvent was evaporated in vacuo. The residue was purified by flash chromatography to give the products.

III. General Procedures of the Desilylation Reaction by using TBAF

To a degassed solution of 1,3,4-trisubstituted-6-trimethylsilyl-3-hexen-1,5-diynes (1 mmol) in dry THF (15 mL), TBAF (1.2 mmol) was added to the solution and stirred at 25° C. for 6 hrs, quenched with saturated aqueous NaCl solutions and extracted with EtOAc. The organic layer was separated and dried over MgSO$_4$. After filtration, the solvent was evaporated in vacuo. The residue was purified by flash chromatography to give the products.

IV. General Procedure for Coupling of (Z)-3-hexen-1,5-diyne with Aryl Iodide A degassed solution of (Z)-3-hexen-1,5-diyne (2.3 mmol) in dry ether (5 mL) containing Pd(PPh$_3$) (0.1 mmol) and CuI (0.6 mmol) was added to a solution of aryl iodide (4.5 mmol) containing n-butylamine (5 mmol). The resulting solution was stirred for at 25° C. 6 hrs, quenched with saturated aqueous NH$_4$Cl and Na$_2$CO$_3$ solutions, and extracted with EtOAc. The organic layer was separated and dried over MgSO$_4$. After filtration, the solvent was evaporated in vacuo. The residue was purified by flash chromatography to give the products.

Example 1

Synthesis of 4-trimethylsilyl-1-chorobuten-3-yne (a1)

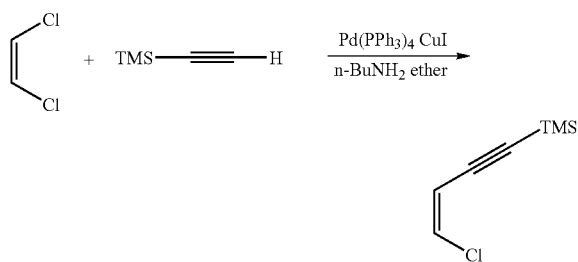

4-trimethylsilyl-1-chorobuten-3-yne (a1) was synthesized using cis-1,2-dichloroethylene and (trimethylsilyl)acetylene as the starting materials according to Method A of the above-described General Synthesis Procedures I, and gives a brown oil in 40% yield.

Example 2

Synthesis of 2-(2-trimethylsilyl-1-ethynyl)iodobenzene (a2)

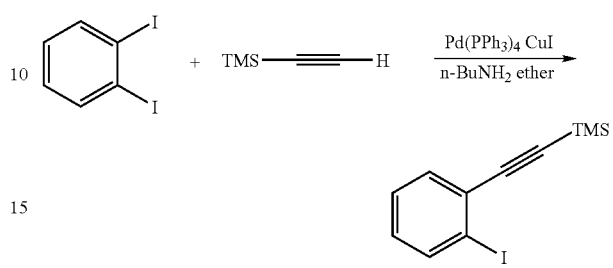

The title compound was synthesized as a yellow oil in 54% yield using 1,2-diiodobenzene and (trimethylsilyl)acetylene as the starting materials according to Method A of the above-described General Synthesis Procedures I.

Example 3

Synthesis of 2-ethynylbenzonitrile (a3)

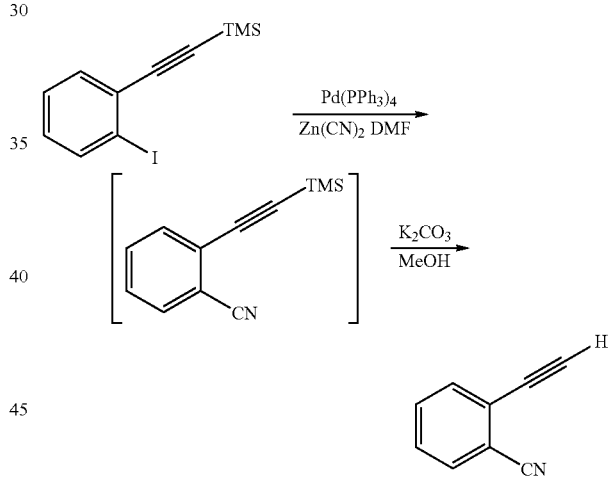

The title compound may be prepared from compound (a2) of Example 2 in two steps according to the above synthesis scheme. According to Method B of the above-described General Synthesis Procedures I, compound (a2) is converted to 2-(2-trimethylsilylethynyl)benzonitrile, which is then dissolved into dry methanol with K$_2$CO$_3$ to give a white solid in 73% yield (Method C of the above-described General Synthesis Procedures I).

Alternatively, 2-ethynylbenzonitrile (a3) may be prepared according to the procedures set forth in M. J. Wu et al. (1999), *Organic Letters*, 1 (5):767-768, which is incorporated herein by reference in its entirety. Specifically, palladium-catalyzed coupling reaction of trimethylsilylacetylene with 1,2-diiodobenzene produced 2-(2-trimethylsilylethynyl)iodobenzene in 58% yield; 2-(2-trimethylsilylethynyl) iodobenzene was then coupled with Zn(CN)$_2$ using palladium(0) as a catalyst to give 2-(2-trimethylsilylethynyl) benzonitrile in 45% yield; and finally, 2-(2- trimethylsilylethynyl)benzonitrile was treated with tetrabutylammonium fluoride to give 2-ethynylbenzonitrile (a3) in 97% yield.

Example 4

Synthesis of (Z)-1-chloro-1-octen-3-yne (a4)

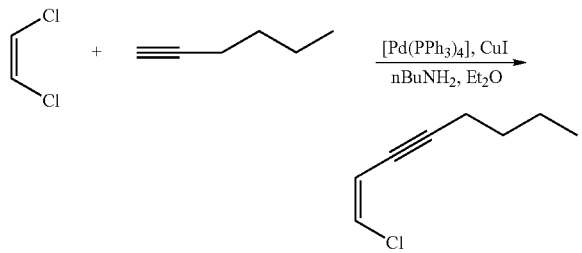

The coupling reaction of cis-1,2-dichloroethylene and 1-hexyne according to Method A of the above-described General Synthesis Procedures I. gave (Z)-1-chloro-1-octen-3-yne (a4) as an oil in 65% yield.

Detected properties of the title compound:
$^1$H NMR (CDCl$_3$, 400 MHz): δ 6.28 (dd, 1H, J=7.3, 0.4 Hz), 5.84 (dt, 1H, J=7.3, 2.2 Hz), 2.38 (td, 2H, J=7.0, 2.2 Hz), 1.59-1.42 (m, 4H), 0.92 (t, 3H, J=7.3 Hz). MS (EI): 142 (M$^+$, 32), 86 (53), 49 (56), 35 (25). HRMS (EI) calcd for C$_8$H$_{11}$Cl: 142.0548, found 142.0550.

Example 5

Synthesis of 1-trimethylsilyl-dec-3-ene-1,5-diyne (a5)

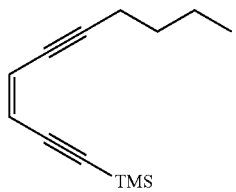

According to Method A of the above-described General Synthesis Procedures I, the coupling reaction of compound (a4) from Example 4 with trimethylsilylacetylene using palladium as a catalyst gave the title compound (a5) as an oil in 53% yield.

Detected properties of the title compound:
$^1$H NMR (CDCl$_3$, 200 MHz): δ 8.81-8.71 (m, 2H), 2.41 (t, 2H, J=6.8 Hz), 1.56-1.44 (m, 4H), 0.92 (t, 3H, J=6.8 Hz), 0.19 (s, 9H). $^{13}$C NMR (CDCl$_3$, 50 MHz): δ 121.5, 118.1, 102.2, 101.7, 99.5, 78.1, 30.7, 21.9, 19.4, 13.6, −0.10. MS (EI): 204 (M$^+$, 91), 189 (100), 145 (32), 131 (28). HRMS (EI) calcd for C$_{13}$H$_{20}$Si: 204.1331, found 204.1335.

Example 6

Synthesis of dec-3-ene-1,5-diyne (a6)

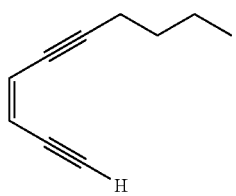

Treatment of compound (a5) from Example 5 with TBAF according Method C of the above-described General Synthesis Procedures I produced the title compound in 80% yield.

Compound (a5) (3.02 g, 14.80 mmol) was dissolved in dry methanol (10 ml), and the solution was stirred with K$_2$CO$_3$ (1.0 g) at room temp. for 1.5 hrs. After the evaporation of methanol in vacuo, the reaction was quenched with saturated aqueous NaHCO$_3$ solution and the resultant solution was extracted with EtOAc. The organic layer was separated and dried over MgSO$_4$. After filtration, the solvent was evaporated in vacuo. The residue was purified by flash chromatography to give the title compound as an oil in 80% yield.

Detected properties of the title compound:
$^1$H NMR (CDCl$_3$, 200 MHz): δ 5.88-5.75 (m, 2H), 3.28 (s, 1H), 2.41 (t, 2H, J=7.0 Hz), 1.58-1.40 (m, 4H), 0.92 (t, 3H, J=7.0 Hz). $^{13}$C NMR (CDCl$_3$, 50 MHz): δ 122.4, 116.9, 99.6, 83.6, 80.9, 77.8, 30.5, 21.8, 19.4, 13.5.

Example 7

Synthesis of Compounds 1-4

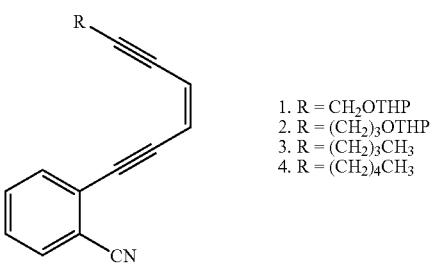

1. R = CH$_2$OTHP
2. R = (CH$_2$)$_3$OTHP
3. R = (CH$_2$)$_3$CH$_3$
4. R = (CH$_2$)$_4$CH$_3$

Compounds 1-4 listed above may be synthesized according to the following scheme, and the detected characteristics thereof are described below.

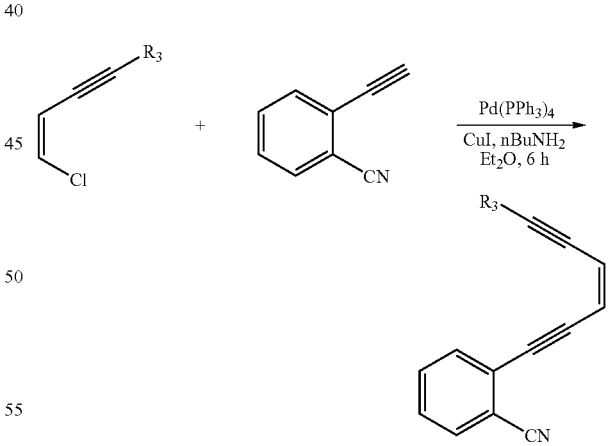

A. 2-(7-(Tetrahydropyranyloxy)-3(Z)-hepten-1,5-diynyl)-benzonitrile 1

Obtained as an oil.
$^1$H NMR (CDCl$_3$, 400 MHz): δ 7.59-7.66 (m, 2H), 7.54 (td, 1H, J=7.5, 1.3 Hz), 7.41 (td, 1H, J=7.5, 1.3 Hz), 6.10 (d, 1H, J=10.8 Hz), 6.02 (td, 1H, J=10.8, 2.0 Hz), 4.87 (t, 1H, J=3.5 Hz), 4.56 (dd, 1H, J=6.3, 1.9 Hz), 4.49 (dd, 1H, J=6.3, 1.9 Hz), 3.82-3.88 (m, 1H), 3.50-3.55 (m, 1H), 1.50-1.83(m, 6H). $^{13}$C NMR (CDCl$_3$, 100 MHz): δ 132.8, 132.7, 132.2, 128.6, 128.5, 121.7, 121.3, 118.6, 96.8, 94.8, 92.7, 92.5, 82.9, 61.9, 55.0, 51.0, 30.2, 25.3, 18.9. MS (EI) [m/z (relativeintensity)]: 291 (M+, 1.8), 190 (100), 85 (45). HRMS calcd for $C_{19}H_{17}NO_2$: 291.1260, found 291.1255.

B. 2-(9-(Tetrahydropyranyloxy)-3(Z)-nonen-1,5-diynyl)-benzonitrile 2

Obtained as an oil.

$^1$H NMR (CDCl$_3$, 400 MHz): δ 7.67-7.63 (m, 2H), 7.58-7.50 (m, 2H), 7.43-7.35 (m, 2H), 6.03 (d, 1H, J=10.9 Hz), 5.96 (dt, 1H, J=10.9, 1.7 Hz), 4.58 (t, 1H, J=3.8 Hz), 3.90-3.76(m, 2H), 3.57-3.46 (m, 2H), 2.60 (td, 2H, J=7.3, 1.7 Hz), 1.95-1.48 (m, 8H). $^{13}$C NMR (CDCl$_3$, 100 MHz): δ 132.8, 132.7, 132.6, 132.4, 132.2, 128.4, 122.5, 117.1, 115.0, 100.4, 98.7, 93.2, 91.7, 78.3, 66.0, 62.1, 30.6, 28.7, 25.4, 19.5, 16.8; MS (EI) [m/z(relative intensity)] 319 (M+, 11), 235 (68), 216 (100), 203 (38), 190 (71). HRMS calcd for $C_{21}H_{21}NO_2$: 319.1573, found 319.1576.

C. 2-(3(Z)-Decen-1,5-diynyl)benzonitrile 3

Obtained as an oil.

$^1$H NMR (CDCl$_3$, 400 MHz): δ 7.66 (dd, 1H, J=7.8, 1.0 Hz), 7.59-7.49 (m, 2H), 7.43-7.35 (m, 1H), 6.03-5.98 (m, 2H), 2.47 (td, 2H, J=6.8, 1.5 Hz), 1.61-1.39 (m, 4H), 0.89 (t, 3H, J=7.0 Hz). $^{13}$C NMR (CDCl3, 100 MHz): δ 132.7, 132.6, 132.2, 128.3, 127.1, 122.7, 117.3, 116.9, 115.0, 101.2, 93.3, 91.4, 78.1, 30.6, 21.9, 19.6, 13.6. MS (EI) [m/z (relative intensity)]: 233 (M+, 22), 218 (55), 204 (100), 190 (73), 164 (36); HRMS calcd for $C_{17}H_{15}N$: 233.1205, found 233.1210.

D. 2-(3(Z)-Undecen-1,5-diynyl)benzonitrile 4

Obtained as an oil.

$^1$H NMR (CDCl$_3$, 400 MHz): δ 7.67 (dd, 1H, J=7.2, 1.1 Hz), 7.57-7.53 (m, 2H), 7.49-7.36 (m, 1H), 6.06-5.99 (m, 2H), 2.47 (td, 2H, J=6.9, 1.5 Hz), 1.64-1.25 (m, 6H), 0.85 (t, 3H, J) 6.8 Hz). $^{13}$C NMR (CDCl$_3$, 100 MHz): δ 132.7, 132.6, 132.2, 128.3, 127.1, 122.7, 117.3, 116.9, 115.0, 101.3, 93.3, 91.4, 78.1, 31.0, 28.2, 22.2, 19.9, 13.9. MS (EI) [m/z (relative intensity)]: 247 (M+, 14), 217 (49), 204 (100), 190 (68); HRMS calcd for $C_{18}H_{17}N$: 247.1362, found 247.1357.

Example 8

Synthesis of 2-(6-phenyl-3(Z)-hexen-1,5-diynyl)benzonitrile 5

The Title compound may be produced from compound a3 of Example 3 and 4-chloro-1-phenyl-3-buten-1-yne according to the procedures for the production of compounds 1-4 as set forth in Example 7.

Example 9

Synthesis of (3Z)-Decen-1,5-diynylbenzene 6

The Title compound may be produced by the coupling reaction of compound a6 from Example 6 and iodobenzene according to the above-described General Procedures IV. Alternatively, the Title compound may be produced from compound a4 of Example 4 and phenylacetylene according to the procedures for the production of compounds 1-4 as set forth in Example 7.

Detected properties of the title compound:

Obtained as an oil in 67% yield.

$^1$H NMR (CDCl$_3$, 200 MHz): δ 7.49-7.43 (m, 2H), 7.35-7.29 (m, 3H), 5.94 (d, 1H, J=10.8 Hz), 5.87 (d, 1H, J=10.8 Hz), 2.45 (t, 2H, J=6.8 Hz), 1.63-1.43 (m, 4H), 0.9 (t, 3H, J=7.0 Hz). $^{13}$C NMR (CDCl$_3$, 50 MHz): δ 131.7 128.3, 128.2, 123.2, 120.3, 118.1, 99.4, 96.0, 87.2, 78.4, 30.7, 21.9, 19.5, 13.6. MS (EI) [m/z (relative intensity)]: 208 (M+, 67), 179 (26), 178 (63), 165 (100), 163 (28), 152 (27), 139 (39), 115 (28). HRMS calcd for $C_{16}H_{16}$, Mr=208.1255, found 208.1252.

Example 10

Synthesis of 2-(2-(2-Alkynylphenyl)ethynyl)benzonitriles 7-10

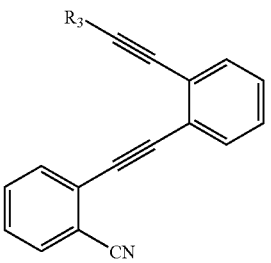

$R_3$ = THPOCH$_2$
$R_3$ = THPO(CH$_2$)$_3$
$R_3$ = Me(CH$_2$)$_3$
$R_3$ = Me(CH$_2$)$_4$ 2-(2-(2-Alkynylphenyl)ethynyl)benzonitriles 7-10 may be synthesized by the coupling reaction of 2-ethynylbenzonitrile (a3) and corresponding 2-(2-sustituted-1-ethynyl) iodobenzenes according to the aforesaid Scheme 4. The obtained yields varied from 40% to 98%.

Specifically, a degassed solution of a selected 2-alkynyliodobenzene (12 mmol) in dry ether (30 mL) containing Pd(PPh$_3$)$_4$ (0.8 mmol) and CuI (3.2 mmol) was added to a solution of 2-ethynylbenzonitrile (24 mmol) containing n-butylamine (34 mmol). The resulting solution was stirred at 25° C. for 6 hrs, quenched with saturated aqueous NH$_4$Cl and Na$_2$CO$_3$ solutions, and extracted with EtOAc. The organic layer was separated and dried over MgSO$_4$. After filtration, the solvent was evaporated in vacuo. The residue was purified by flash chromatography to give the product.

A. 2-(2-(3-Tetrahydro-pyranyl-5-oxy-1-propynylphenyl)ethynyl)benzonitrile 7

Obtained as an oil in 98% yield.

$^1$H NMR (CDCl$_3$, 200 MHz): δ 7.84-7.37 (m, 8H), 5.08-5.04 (m, 1H), 4.70 (d, 2H, J=2.2 Hz), 4.21-3.93 (m, 1H), 3.69-3.61 (m, 1H). 1.93-1.58 (m, 6H). $^{13}$C NMR (CDCl$_3$, 50 MHz): δ 132.7, 132.6, 132.5, 132.3, 132.2, 128.9, 128.4, 128.2, 127.1, 125.6, 124.9, 117.4, 115.1, 96.8, 94.4, 89.1, 84.0, 61.9, 54.9, 30.3, 25.4, 19.0. HRMS (EI) calcd for $C_{23}H_{19}NO_2$: 341.1414, found 341.1452.

B. 2-(2-(3-Tetrahydro-pyranyl-5-oxy-1-pentynylphenyl)ethynyl)benzonitrile 8

Obtained as an oil in 89% yield.

$^1$H NMR (CDCl$_3$, 200 MHz): δ 7.70-7.51 (m, 4H), 7.47-7.34 (m, 2H), 7.31-7.28 (m, 2H), 4.59-4.56 (m, 1H), 3.95-3.81 (m, 1H), 3.62-3.47 (m, 1H), 2.64 (t, 2H, J=7.4 Hz), 1.97-1.46 (m, 10H). $^{13}$C NMR (CDCl$_3$, 50 MHz): δ 132.7, 132.6, 132.5, 132.3, 132.1, 132.0, 128.9, 128.2, 127.4, 127.3, 126.4, 124.3, 117.5, 115.2, 98.8, 94.9, 88.6, 79.3, 66.1, 62.2, 30.7, 28.9, 25.5, 19.5, 16.6. HRMS (EI) calcd for $C_{25}H_{23}NO_2$: 369.1725, found 369.1729.

C. 2-(2-(2-Hexynylphenyl)ethynyl)benzonitrile 9

Obtained as an oil in 62% yield.

$^1$H NMR (CDCl$_3$, 200 MHz): δ 7.71-7.52 (m, 4H), 7.47-7.37 (m, 2H), 7.33-7.25 (m, 2H), 2.52 (t, 2H, J=7.6 Hz), 1.66-1.43 (m, 4H), 0.89 (t, 3H, J=7.6 Hz). HRMS (EI) calcd for $C_{21}H_{17}N$: 283.1326, found 283.1326.

D. 2-(2-(2-Heptynylphenyl)ethynyl)benzonitrile 10

Obtained as an oil in 40% yield.

$^1$H NMR (CDCl$_3$, 200MHz): δ 7.70-7.53 (m, 4H), 7.47-7.34 (m, 2H), 7.30-7.25 (m, 2H), 2.51 (t, 2H, J=7.6 Hz), 1.69-1.25 (m, 6H), 0.85 (t, 3H, J=7.6 Hz). HRMS (EI) calcd for C$_{21}$H$_{17}$N: 297.1515, found 297.1518.

Example 11

Synthesis of 1,4-Bis-(3-(Z)-Dodecen-1,5-diynyl) benzene 11 and 4,4'-Bis-(3-(Z)-Dodecen-1,5-diynyl) biphenyl 12

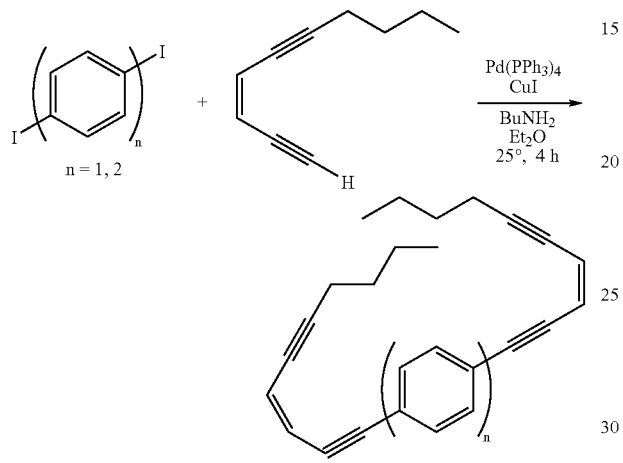

The title compounds 11 and 12 may be respectively produced by the coupling reaction of compound a6 from Example 6 and 1,4-diiodobenzene and 4,4'-diiodobiphenyl according to the above scheme.

A. 1,4-Bis-(3-(Z)-Dodecen-1,5-diynyl)benzene 11

Obtained as an oil in 78% yield.

$^1$H NMR (CDCl$_3$, 200 MHz): δ 7.41 (s, 2H), 6.02-5.58 (m, 4H), 2.45 (t, 2H, J=7.2 Hz), 1.70-1.47 (m, 8H), 0.90 (t, 6H, J=7.2 Hz). $^{13}$C NMR (CDCl$_3$, 50 MHz): δ 131.5, 122.2, 120.8, 117.9, 99.9, 95.7, 89.2, 78.4, 30.7, 21.9, 19.6, 13.6. HRMS (EI) calcd for C$_{26}$H$_{26}$: 338.2035, found 338.2017.

B. 4,4'-Bis-(3-(Z)-Dodecen-1,5-diynyl)biphenyl 12

Obtained as an oil in 51% yield.

$^1$H NMR (CDCl$_3$, 200 MHz): δ 7.58-7.51 (m, 8H), 5.98-5.86 (m, 4H), 2.45 (td, 4H, J=7.2, 2.0 Hz), 1.65-1.48 (m, 8H), 0.91 (t, 6H, J=7.4 Hz). $^{13}$C NMR (CDCl$_3$, 50 MHz): δ 140.1, 132.2, 126.85, 122.6, 120.4, 116.1, 99.6, 95.9, 88.3, 78.5, 31.5, 30.7, 21.9, 14.2. HRMS (EI) calcd for C$_{32}$H$_{30}$ 414.2349, found 414.2346.

Example 12

Synthesis of 1-aryl dec-3-ene-1,5-diynes 13-23

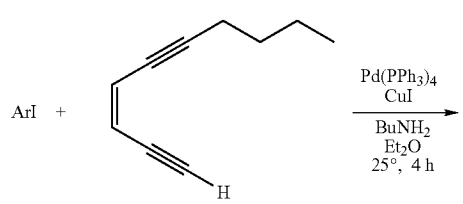

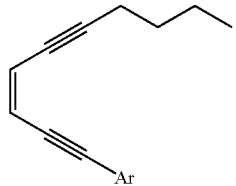

13. Ar = p-ClC$_6$H$_4$
14. Ar = p-CNC$_6$H$_4$
15. Ar = 2-pyridinyl
16. Ar = 2-thienyl
17. Ar = 2-pyrazinyl
18. Ar = p-CF$_3$C$_6$H$_4$
19. Ar = m-CF$_3$C$_6$H$_4$
20. Ar = o-CF$_3$C$_6$H$_4$
21. Ar = p-NO$_2$C$_6$H$_4$
22. Ar = o-CH$_3$CO$_2$C$_6$H$_4$
23. Ar = p-CH$_3$COC$_6$H$_4$ A series of 1-aryl dec-3-ene-1,5-diynes 12-23 may be produced by the coupling reaction of compound a6 from Example 6 and aryl iodides according to the above-described General Procedures IV.

A. 4-(3-(Z)-Dodecen-1,5-diynyl)benzochloride 13

Obtained as an oil in 31%.

$^1$H NMR (CDCl$_3$, 200 MHz): δ 7.36 (d, 2H, J=8.8 Hz), 7.31 (d, 2H, J=8.6 Hz), 5.97-5.84 (m, 2H), 2.45 (t, 2H, J=6.8 Hz), 1.61-1.45 (m, 4H), 0.9 (t, 3H, J=7.0 Hz). $^{13}$C NMR (CDCl$_3$, 50MHz): δ 134.4, 132.8, 128.6, 121.7, 120.7, 117.7, 99.7, 94.7, 88.1, 78.3, 30.7, 21.8, 19.5, 13.5. MS (EI) 242 (M$^+$, 100), 201 (16), 199 (40), 192 (78), 165 (63), 164 (45), 163 (52). HRMS (EI) calcd for C$_{16}$H$_{15}$Cl: 242.0859, found 242.0863.

B. 4-(3-(Z)-Dodecen-1,5-diynyl)benzonitrile 14

Obtained as an oil in 46%.

$^1$H NMR (CDCl$_3$, 200 MHz): δ 7.61 (d, 2H, J=6.4 Hz), 7.53 (d, 2H, J=8.4 Hz), 5.95 (d, 2H, J=1.6 Hz), 2.44 (t, 2H, J=6.8 Hz), 1.59-1.44 (m, 4H), 0.9 (t, 3H, J=7.2 Hz). $^{13}$C NMR (CDCl$_3$, 50 MHz): δ 132.0, 131.9, 128.1, 122.2, 118.4, 117.1, 111.5, 100.6, 93.9, 91.3, 78.2, 30.5, 21.8, 19.4, 13.5. MS (EI) 233 (M$^+$, 51), 203 (51), 190 (100), 177 (35), 164 (46), 140 (28). HRMS (EI) calcd for C$_{17}$H$_{15}$N: 233.1206, found 233.1205.

C. 2-(3-(Z)-Dodecen-1,5-diynyl)pyridine 15

Obtained as an oil in 84% yield.

$^1$H NMR (CDCl$_3$, 200 MHz): δ 8.58 (dt, 1H, J=5.0, 1.0 Hz), 7.63 (td, 1H, J=7.6, 1.8 Hz), 7.42 (td, 1H, J=7.6, 1.0 Hz), 7.23-7.16 (m, 2H), 5.99-5.93 (m, 2H), 2.43 (td, 2H, J=7.0, 1.6 Hz), 1.92-1.43 (m, 4H), 0.87 (t, 3H, J=7.0 Hz). $^{13}$C NMR (CDCl$_3$, 50 MHz): δ 150.5, 143.3, 135.9, 127.2, 122.7, 122.1, 117.3, 100.3, 94.7, 86.8, 78.2, 30.6, 21.8, 19.5, 13.5. MS (EI): 209 (M$^+$, 19), 180 (100), 78 (18), 51 (18). HRMS (EI) calcd for C$_{15}$H$_{15}$N: 209.1209, found 209.1205.

D. 2-(3-(Z)-Dodecen-1,5-diynyl)thiophene 16

Obtained as an oil in 53% yield.

$^1$H NMR (CDCl$_3$, 200 MHz): δ 7.29 (d, 1H, J=5.2 Hz), 7.22 (d, 1H, J=2.6 Hz), 7.00 (t, 1H, J=5.2 Hz), 5.94 (d, 1H, J=10.4 Hz), 5.86 (d, 1H, J=10.8 Hz), 2.45 (d, 2H, J=6.8 Hz), 1.63-1.47 (m, 4H), 0.92 (t, 3H, J=6.8 Hz). $^{13}$C NMR (CDCl$_3$, 50 MHz): δ 132.1, 127.7, 127.2, 123.3, 120.1, 117.7, 99.8, 91.2, 89.1, 78.4, 30.6, 21.9, 19.5, 13.5. MS (EI): 214 (M$^+$, 100), 184 (41), 171 (80), 165 (53). HRMS (EI) calcd for C$_{14}$H$_{14}$S: 214.0811, found 214.0817.

E. 2-(3-(Z)-Dodecen-1,5-diynyl)pyrazine 17

Obtained as an oil in 99% yield.

$^1$H NMR (CDCl$_3$, 200 MHz): δ 8.66 (d, 1H, J=1.6 Hz), 8.55 (s, 1H), 8.45 (d, 1H, J=2.4 Hz), 5.98 (m, 2H), 2.44 (t, 2H, J=6.8 Hz), 1.58-1.43 (m, 4H), 0.88 (t, 3H, J=7.0 Hz). $^{13}$C NMR (CDCl$_3$, 50 MHz): δ 147.8, 144.4, 142.6, 140.3, 123.5, 116.5, 101.3, 91.7, 90.8, 78.1, 30.5, 21.8, 19.5, 13.5. MS (EI): 210 (M$^+$, 39), 181 (100), 168 (14), 127 (17). HRMS (EI) calcd for C$_{14}$H$_{14}$N$_2$: 210.1154, found 210.1158.

F. 4-(3-(Z)-Dodecen-1,5-diynyl)trifluoromethylbenzene 18

Obtained as an oil in 46% yield.

$^1$H NMR (CDCl$_3$, 200 MHz): δ 7.57 (s, 4H), 5.95 (d, 2H, J=1.6 Hz), 2.46 (t, 2H, J=6.8 Hz), 1.58-1.49 (m, 4H), 0.90 (t, 3H, J=7.0 Hz). $^{13}$C NMR (CDCl$_3$, 50 MHz): δ 146.9, 134.6, 131.8, 127.0, 125.3, 121.6, 117.4, 112.1, 100.2, 89.4, 78.3, 30.6, 21.9, 19.5, 13.5. MS (EI): 276 (M$^+$, 100), 233 (59), 207 (31), 192 (24), 165 (47), 49 (43). HRMS (EI) calcd for C$_{17}$H$_{15}$F$_3$: 276.1129, found 276.1174.

G. 3-(3-(Z)-Dodecen-1,5-diynyl)trifluoromethylbenzene 19

Obtained as an oil in 46% yield.

$^1$H NMR (CDCl$_3$, 200 MHz): δ 7.72 (s, 1H), 7.61 (d, 1H, J=7.6 Hz), 7.55 (d, 1H, J=8.0 Hz), 7.45 (t, 1H, J=7.6 Hz), 5.97 (d, 1H, J=10.8 Hz), 5.92 (d, 1H, J=10.8 Hz), 2.46 (t, 2H, J=6.8 Hz), 1.62-1.45 (m, 4H), 0.90 (t, 3H, J=7.2 Hz). $^{13}$C NMR (CDCl$_3$, 50 MHz): δ 146.9, 134.6, 128.8, 128.5, 124.8, 124.8, 124.2, 121.5, 117.4, 100.1, 94.2, 88.6, 78.3, 30.6, 21.8, 19.5, 13.4. MS (EI): 276 (M$^+$, 100), 261 (30), 246 (34), 233 (84), 207 (47), 183 (62), 178 (37), 165 (68). HRMS (EI) calcd for C$_{17}$H$_{15}$F$_3$: 276.1125, found 276.1127.

H. 2-(3-(Z)-Dodecen-1,5-diynyl)trifluoromethylbenzene 20

Obtained as an oil in 33% yield.

$^1$H NMR (CDCl$_3$, 200 MHz) δ 7.64 (td, 2H, J=7.8, 1.8 Hz), 7.39-7.37 (m, 2H) 6.02-5.87 (m, 2H) 2.45 (t, 2H, J=7.0 Hz), 1.60-1.51 (m, 4H) 0.90 (t, 3H, J=7.0 Hz).; $^{13}$C NMR (CDCl$_3$, 50 MHz) δ 146.3, 134.2, 131.2, 128.0, 125.8, 125.7, 121.6, 117.5, 112.1, 100.3, 92.5, 91.5, 78.0, 30.6, 21.9, 19.5, 13.5. MS (EI) 276 (M$^+$, 100), 233 (34), 232 (29), 221 (48), 214 (22), 183 (29), 165 (14). HRMS (EI) calcd for C$_{17}$H$_{15}$F$_3$ 276.1174, found 276.1174.

I. 4-nitro-1-(3-(Z)-dodecen-1,5-diynyl)benzene 21

Obtained as an oil in 59% yield.

$^1$H NMR (CDCl$_3$, 200 MHz): δ 8.16 (d, 2H, J=9.0 Hz), 7.60 (d, 2H, J=9.0 Hz), 5.97 (s, 2H), 2.45 (t, 2H, J=6.4 Hz), 1.61-1.45 (m, 4H), 0.9 (t, 3H, J=7.0 Hz). $^{13}$C NMR (CDCl$_3$, 50 MHz): δ 147.0, 132.1, 123.5, 122.6, 118.3, 117.0, 100.9, 93.6, 92.2, 78.2, 30.6, 21.8, 19.5, 13.5. MS (EI): 253 (M$^+$, 100), 238 (16), 210 (16), 192 (14), 165 (13), 163 (21). HRMS (EI) calcd for C$_{16}$H$_{15}$NO$_2$: 253.1105, found 253.1103.

J. 2-(3-(Z)-Dodecen-1,5-diynyl)benzoate 22

Obtained as an oil in 31% yield.

$^1$H NMR (CDCl$_3$, 200 MHz): δ 7.95 (d, 1H, J=7.8 Hz), 7.57 (d, 1H, J=7.4 Hz), 7.46-7.31 (m, 2H), 6.00 (d, 1H, J=10.8 Hz), 5.91 (d, 1H, J=10.8 Hz), 3.91 (s, 2H), 2.45 (t, 2H, J=6.8 Hz), 1.62-1.42 (m, 4H), 0.87 (t, 3H, J=7.0 Hz). $^{13}$C NMR (CDCl$_3$, 50 MHz): δ 166.5, 134.3 131.6, 131.5, 130.3, 127.9, 123.7, 120.8, 118.1, 99.6, 94.6, 78.4, 52.0, 30.6, 21.9, 19.5, 13.5. MS (EI): 266 (M$^+$, 71), 237 (75), 224 (51), 223 (70), 209 (82), 191 (21), 181 (49), 176 (24). HRMS (EI) calcd for C$_{18}$H$_{18}$O$_2$: 266.1305, found 266.1307.

K. 4-(3-(Z)-Dodecen-1,5-diynyl)acetophenone 23

Obtained as an oil in 96% yield.

$^1$H NMR (CDCl$_3$, 200 MHz): δ 7.92 (d, 2H, J=8.4 Hz), 7.54 (d, 2H, J=8.4 Hz), 5.99-5.90 (m, 2H), 2.60 (s, 3H), 2.45 (t, 2H, J=7.2 Hz), 1.63-1.46 (m, 4H), 0.91 (t, 3H, J=7.2 Hz). $^{13}$C NMR (CDCl$_3$, 50MHz): δ 197.2, 136.3, 131.7, 128.2, 128.1, 121.6, 117.6, 100.3, 95.0, 90.4, 78.4, 30.7, 26.6, 21.9, 19.5, 13.6. MS (EI): 250 (M$^+$, 100), 235 (37), 165 (29). HRMS (EI) calcd for C$_{18}$H$_{18}$O: 250.1372, found 250.1358.

Example 13

Synthesis of 2-(3-hexen-1,5-diyne)benzonitrile

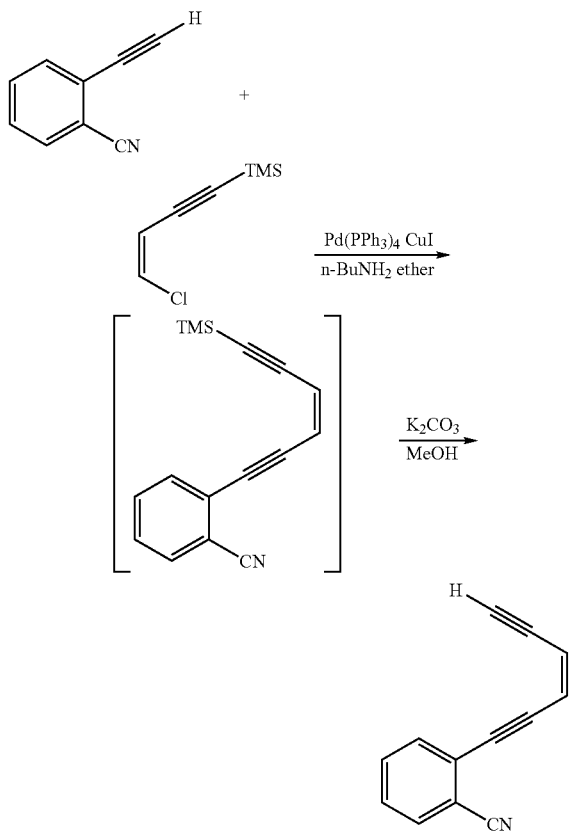

The Title compound may be produced in two steps using compound a1 Example 1 and compound a3 from Example 3 as starting materials. Firstly, compound a1 and compound a3 were reacted according to Method A set forth in the above-described General Synthesis Procedures I to form 2-(6-trimethylsilyl-3-hexen-1,5-diynyl)benzonitrile, which was subsequently dissolved into dry methanol with K$_2$CO$_3$ to give a brown oil in 53% yield.

Example 14

Synthesis of 2-(6-aryl-3-hexen-1,5-diynyl)benzonitriles 24-33

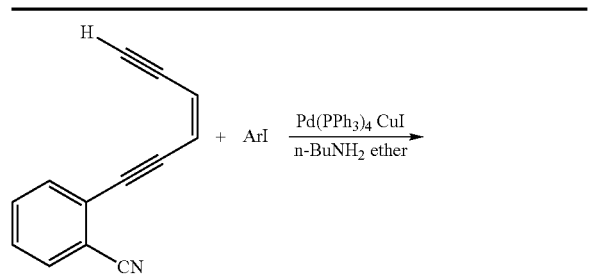

| Reaction Product | Aryl group | Yield (%) |
|---|---|---|
| 24 2-(6-(2-xylenyl)-3-hexen-1,5-diyne)benzonitrile brown oil | H₃C, CH₃ (2,3-dimethylphenyl) | 55 |
| 25 2-(6-(4-anisyl)-3-hexen-1,5-diynyl)benzonitrile brown oil | OCH₃ (4-methoxyphenyl) | 45 |
| 26 2-(6-(2-anisyl)-3-hexen-1,5-diynyl)benzonitrile brown oil | H₃CO (2-methoxyphenyl) | 43 |
| 27 2-(6-(2-pyridinyl)-3-hexen-1,5-diynyl)benzonitrile brown oil | 2-pyridinyl | 53 |
| 28 2-(6-(4-tolyl)-3-hexen-1,5-diynyl)benzonitrile brown oil | CH₃ (4-methylphenyl) | 90 |

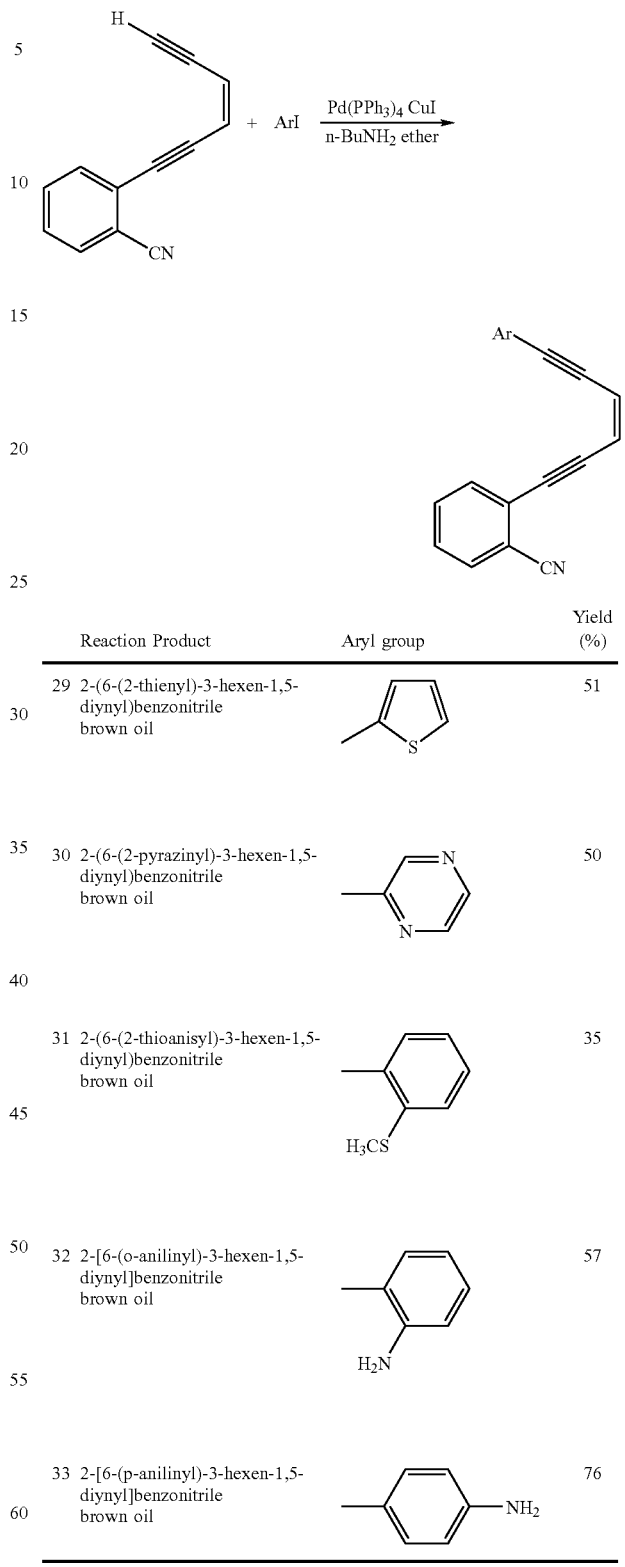

| Reaction Product | Aryl group | Yield (%) |
|---|---|---|
| 29 2-(6-(2-thienyl)-3-hexen-1,5-diynyl)benzonitrile brown oil | 2-thienyl | 51 |
| 30 2-(6-(2-pyrazinyl)-3-hexen-1,5-diynyl)benzonitrile brown oil | 2-pyrazinyl | 50 |
| 31 2-(6-(2-thioanisyl)-3-hexen-1,5-diynyl)benzonitrile brown oil | H₃CS (2-methylthiophenyl) | 35 |
| 32 2-[6-(o-anilinyl)-3-hexen-1,5-diynyl]benzonitrile brown oil | H₂N (2-aminophenyl) | 57 |
| 33 2-[6-(p-anilinyl)-3-hexen-1,5-diynyl]benzonitrile brown oil | NH₂ (4-aminophenyl) | 76 |

The above-indicated 2-(6-aryl-3-hexen-1,5-diynyl)benzonitriles 24-33 may be produced by the coupling reaction of 2-(3-hexen-1,5-diyne)benzonitrile from Example 13 with various aryl iodides.

Example 15

Synthesis of Compounds 34-43

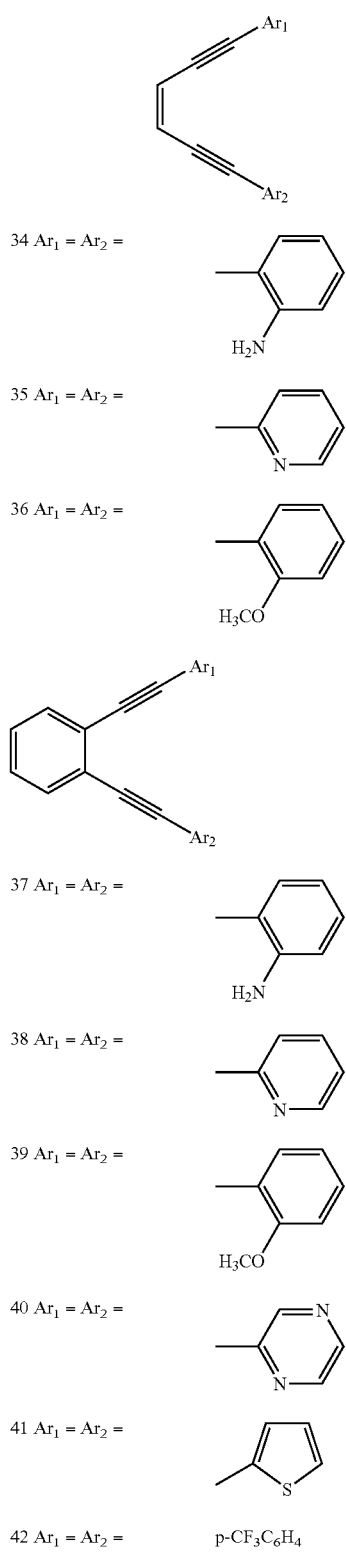

The above-indicated 1,6-diaryl-3-hexen-1,5-diynes 34-43 may be produced by the coupling reaction of 1,2-disubstituted-dihaloethene with a selected 2-aryl-1-ethyne. Specifically, a degassed solution of 1,2-disubstituted-dihaloethene (12 mmol) in dry ether (30 mL) containing $Pd(PPh_3)_4$ (0.8 mmol) and CuI (3.2 mmol) was added to a solution of the selected 2-aryl-1-ethyne (24 mmol) containing n-butylamine (34 mmol). The resulting solution was stirred at 25° C. for 4 hrs, quenched with saturated aqueous $NH_4Cl$ and $Na_2CO_3$ solutions, and extracted with EtOAc. The organic layer was separated and dried over $MgSO_4$. After filtration, the solvent was evaporated in vacuo. The residue was purified by flash chromatography to give the products.

Pharmacological Examples

In order to determine the biological activities of the aryl-substituted acyclic enediynes 1-43 of formula (I) according to the present invention, the following pharmaceutical activity assay was performed.

General Procedures

A. In Vitro Anticancer Assay (Cytotoxicity):

The cytotoxicities of Compounds were evaluated using five human solid tumor cells (KB, Hela, DLD, NCI, and Hepa) and/or the NCI's full panel of 60 human cancer cell lines derived from nine cancer cell types, including: leukemia (CCRF-CEM, HL-60 (TB), MOLT-4, K-562, RPMI-826, and SR); non-small cell lung cancer (A549/ATCC, EKVX, HOP-62, HOP-92, $NC_1$-H226, $NC_1$-H23, $NC_1$-H332M, $NC_1$-H460, and $NC_1$-H522); colon cancer (COLO 205, HCC-2998, HCT-116, HCT-15, HT29, KM12, and SW-620); CNS cancer (SF-268, SF-295, SF-539, SNB-19, SNB-75, and U251); melanoma (LOX IMVI, MALME-3M, M14, SK-MEL-2, SK-MEL-28, SK-MEL-5, UACC-62, and UACC-257); ovarian cancer (IGROV1, OVCAR-3, OVCAR-4, OVCAR-5, OVCAR-8, and SK-OV-3); renal cancer (786-0, ACHN, CAKI-1, RXF 393, SN12C, TK-10, and UO-31); prostate cancer (PC-3 and DU-145); and breast cancer (MCF7, MCF7/ADR-RES, MDA-MB-231/ATCC, HS 578T, MDA-MB-435, MDA-N, and T-47D).

For each compound, dose-response curves for each tumor cell were measured with five different drug concentrations, and the concentrations causing 50% cell-growth inhibition ($GI_{50}$) compared with the control were calculated (A. Monks, D. Scudiero, P. Skehaan, R. Shoemaker, K. Paull, D. Vistica, C. Hose, J. Langley, P. Cronise, A. Vaigro-Wolff, M. Gray-Goodrich, H. Campbell, J. Mayo, M. Boyd, *J. Natl. Cancer Inst.* 1991, 83, 757).

B. General Topoisomerase I Course Assay:

All samples were kept in 23 μl total volume; (a) negative control (DNA alone): contained 10× Topo I buffer (2 μl) and pGEM9zf(−) DNA (1 μg/μl), 0.1% BSA (2 μl) and d-$H_2O$ (18 μl); (b) positive control (DNA+Topo I): contained 10× Topo I buffer (2 μl) and pGEM9zf(−) DNA (1 μg/μl), 1 units/μl of topoisomerase I, 0.1% BSA (2 μl) and d-$H_2O$ (17

μl); (c) camptothecin control (DNA+Topo I+camptothecin): contained 10× Topo I buffer (2 μl) and pGEM9zf(−) DNA (1 μg/μl), 1 units/μl of topoisomerase I, 0.1% BSA (2 μl), d-H$_2$O (15 μl) and camptothecin (2 μl, dissolved in DMSO, final conc. of DMSO was 8.7% v/v); (d) experiments for compounds 7-10, 11-12 and 13-23 (DNA+Topo I+compounds): contained 10× Topo I buffer (2 μl) and pGEM9zf(−) DNA(I1 μg/μl), 1 units/μl of topoisomerase I, 0.1% BSA (2 μl), d-H$_2$O (15 μl) and compounds (2 μl, dissolved in DMSO, final conc. of DMSO was 8.7% v/v). (a)-(d) were well-mixed before incubation. The tubes were incubated in 37° C. water bath for 30 min.

C. Gel Electrophoresis:

The reaction mixtures were proceeded by using 2% agarose gel in standard TBE buffer (1×, 0.06 M Tris, 0.06 M boric acid, 0.5 M EDTA), which had previously been added 2 μl of loading buffer containing 0.25% bromophenol blue, 0.25% xylene cyanol, 5% SDS, and 0.25% sucrose. The gels were run at 50 volts for 1.5 hr, and stained with ethidium bromide for 20 min. Then, after placing in a UV box, photographic images were made of the gels, using Polaroid 665 films.

D. Cell Cycle Analysis:

Samples of 1×10$^6$ Hep G2 cells were plated on a 6 cm tissue culture dish, and the cells were allowed to recover 24 hrs before any treatment. Thereafter, DMSO or a test compound (1 μM, 10 μM or 50 μM) was added to the cells for 1 hr in complete medium at 37° C., washed twice with PBS, and incubated in fresh media for the incubation time. Cell were harvested with trypsin and washed twice with PBS. Samples were fixed in 70% ethanol and stored at 4° C. for at least 24 hrs and then washed once with McIlvaine's buffer (0.2M Na$_2$HPO$_4$, 0.1M citric acid, pH=7.5) and once again with PBS. Samples were stained with PI (propidium iodide) staining solution (PBS containing 100 μg/ml, RNase A and 10 μg/ml PI [Sigma]), processed on a Coulter Elite flow cytometry, and the data analyzed with the Mutiplus AV program.

Results and Discussion

A. Cytotoxicity:

Compounds of this invention were subjected to in vitro assay to determine whether or not they exhibit the activity of inhibiting the growth of any of five human solid tumor cells (KB, Hela, DLD, NCI, and Hepa) and/or the NCI's full panel of 60 human tumor cell lines derived from 9 cancer cell types.

The IC$_{50}$ values of compounds 1-23 with five human solid tumor cells (KB, Hela, DLD, NCI, and Hepa) are summarized in Table 2. It can be seen from Table 2 that 2-(6-substituted-3-hexen-1,5-diynyl)benzonitriles 1-5 demonstrated to have a tendency of inhibiting the growth of Hepa cell. Among these 23 compounds, 2-(6-phenyl-3-hexen-1,5-diynyl)benzonitrile 5 exhibited the highest cytotoxic activity against Hepa cell at 1.09 μg/ml. 2-(2-(2-alkynylphenyl)-ethynyl)-benzonitiles 8-10 and 1-aryl-3-dodecen-1,5-diynes 13-22 also had the same tendency with DLD cell line, in which 4-nitro-1-(3-(Z)-dodecen-1,5-diynyl)-benzene 21 showed selective potency against DLD cell at the low IC$_{50}$ value of 1.66 μg/ml. 2-(3-(Z)-Dodecen-1,5-diynyl)trifluoromethylbenzene 20 was more active than the other derivatives against Hela cell (IC$_{50}$ value=2.15 μg/ml).

TABLE 2

IC$_{50}$ Values [μg/ml] of Cytotoxicities of Compounds 1-23

| Cell Compd | KB | Hela | DLD | NCI | Hepa |
|---|---|---|---|---|---|
| 1 | n.d. | 9.97 | 8.61 | —* | 14.26 |
| 2 | n.d. | 10.62 | — | — | 14.66 |
| 3 | n.d. | — | 5.03 | — | 12.49 |
| 4 | n.d. | 6.38 | — | — | 7.28 |
| 5 | n.d. | — | — | 7.01 | 1.09 |
| 6 | 14.43 | — | — | 7.35 | — |
| 7 | — | — | — | — | — |
| 8 | — | — | 11.65 | — | — |
| 9 | — | — | 8.98 | — | — |
| 10 | — | — | 16.25 | 9.22 | 5.13 |
| 11 | — | — | — | — | — |
| 12 | 5.57 | — | — | — | — |
| 13 | — | 9.83 | 5.22 | 8.00 | — |
| 14 | — | — | 11.93 | — | — |
| 15 | — | — | 5.15 | — | — |
| 16 | — | — | 6.75 | — | — |
| 17 | 5.93 | 5.30 | 3.89 | 9.43 | 12.34 |
| 18 | 4.32 | 5.86 | 5.71 | 11.15 | 17.08 |
| 19 | 6.74 | — | 7.05 | 7.73 | 14.39 |
| 20 | 19.65 | 2.15 | 8.91 | 5.02 | 12.24 |
| 21 | — | — | 1.66 | — | — |
| 22 | — | — | 7.27 | — | — |
| 23 | 11.19 | — | — | 13.13 | — |

*"—" means IC$_{50}$ > 20 μg/ml; the standard of cytotoxicity test is doxorubicin whose ED$_{50}$ ≈ 0.1 μg/ml;
"n.d." means not detectable.
KB: human oral epidermoid carcinoma.
Hela: human cervix epitheloid carcinoma.
DLD (DLD-1): human colon adenocarcinoma.
NCI (NCI-H661): human lung large cell carcinoma.
Hepa: human hepatoma.

From the cytotoxic assay, enediynes 1-5 were shown to have a tendency of cytotoxic activity with Hepa cell, and the longer the alkyl chain, the higher was the revealed cytotoxic activity. When the substituent at 6-position is a phenyl group, it provides the strongest activity against Hepa cell line. In addition, enediynes 13-22 could induce the growth inhibition of DLD cells, and among compounds, compound 21 showed highest biological activity. Comparing the results of derivatives 15 (Ar=pyridinyl) and 17 (Ar=pyrazinyl) shown in Table 2, this suggests that the increase in the number of nitrogen atoms in the aromatic ring gave lower IC$_{50}$ value and wider spectrums of cytotoxicity. Compound 6 and it's dimmer 12 have a similar structure and remain selective toxicity against KB cell.

The 1,6-diaryl-3-hexen-1,5-diynes 24-43 were subjected to a preliminary cytotoxicity test using three tumor cells (Breast cancer cell MCF-7, non-small cell lung cancer cell NC$_1$-H460, and CNS cancer cell SF-286), and the results are shown in Table 3.

TABLE 3

Preliminary cytotoxicity test of compounds 24-43.

| | Growth percentage | | |
|---|---|---|---|
| Compound | Breast cancer cell MCF-7 | Non-small cell Lung cancer cell NCI-H460 | CNS cancer cell SF-268 |
| 24 | 101 | 129 | 111 |
| 25 | 90 | 48 | 91 |
| 26 | 83 | 16* | 92 |
| 27 | 49 | 23* | 83 |

TABLE 3-continued

Preliminary cytotoxicity test of compounds 24-43.

| Compound | Breast cancer cell MCF-7 | Non-small cell Lung cancer cell NCI-H460 | CNS cancer cell SF-268 |
|---|---|---|---|
| 28 | 80 | 96 | 105 |
| 29 | 49 | 34 | 96 |
| 30 | 73 | 8* | 84 |
| 31 | 62 | 100 | 164 |
| 32 | 36 | 8* | 27* |
| 33 | 100 | 94 | 92 |
| 34 | 5* | 1* | 5* |
| 35 | 73 | 49 | 100 |
| 36 | 49 | 102 | 101 |
| 37 | 17* | 1* | 4* |
| 38 | 1* | 2* | 14* |
| 39 | 90 | 105 | 115 |
| 40 | 54 | 23* | 65 |
| 41 | 49 | 9* | 62 |
| 42 | 37 | 78 | 55 |
| 43 | 108 | 98 | 114 |

*Compounds which reduced the growth of any one of the tested tumor cells to approximately 32% or less were subjected to further evaluation using the NCI's full panel of 60 tumor cell lines.

As can be seen from Table 3, compounds 26, 27, 30, 32, 34, 37, 38, 40 and 41 passed the preliminary screening test and, therefore, they were further subjected to the NCI's full panel screen of 60 cancer cell lines. The detail data of the cytotoxic activities of compounds 26, 27, 30, 32, 34, 37, 38, 40 and 41 are outlined in Table 4, 5 and 6, respectively.

TABLE 4

The in vitro anticancer activities of compounds 26, 27, 30 and 32.

| Cancer Cell Line | cytotoxicity ($GI_{50}{}^a/LC_{50}{}^b$ in μM) | | | |
|---|---|---|---|---|
| | 26 | 27 | 30 | 32 |
| Leukemia* | 3.57 | 12.8 | 5.05 | 0.43 |
| K-562 | 3.68/>100 | 4.07/>100 | 4.88/>100 | 0.48/>100 |
| SR | 4.09/>100 | 4.12/>100 | 4.30/>100 | 0.25/>100 |
| Non-Small Cell Lung Cancer* | 11.8 | 19.6 | 11.8 | 1.70 |
| NCI-H23 | 5.61/>100 | 12.3/>52.6 | 15.9/74.2 | 0.8/>100 |
| NCI-H522 | 5.14/>100 | 15.9/84.7 | 14.8/>100 | 0.3/>8.62 |
| Colon Cancer* | 7.54 | 16.3 | 7.54 | 0.47 |
| KM12 | 6.37/>100 | 10.9/80.4 | 4.39/>100 | 0.34/>100 |
| SW-620 | 6.33/>100 | 12.6/80.5 | 6.98/>100 | 0.39/>100 |
| CNS Cancer* | 20.0 | 20.9 | 32.2 | 9.44 |
| SF-295 | 6.57/>100 | 20.1/>100 | 17.6/>100 | 0.24/12.4 |
| U251 | 9.17/>100 | 18.5/79.0 | 36.1/>100 | 0.43/>100 |
| Melanoma* | 13.7 | 14.2 | 18.7 | 0.77 |
| SK-MEL-5 | 2.09/>100 | 2.99/41.6 | 19.6/>100 | 0.44/33.1 |
| UACC-62 | 23.7/>100 | 15.3/89.7 | 16.7/>100 | 0.37/63.0 |
| Ovarian Cancer* | 32.6 | 27.3 | 38.1 | 1.55 |
| IGROV1 | 1.04/>100 | 17.0/79.1 | 46.2/>100 | 0.27/>100 |
| OVCAR-3 | 4.40/>100 | 4.26/56.9 | 16.6/>100 | 0.17/98.4 |
| Renal Cancer* | 14.5 | 21.7 | 27.0 | 0.66 |
| CAKI-1 | 3.73/>100 | 21.8/>100 | 21.6/>100 | 0.13/35.9 |
| SN12C | 26.0/>100 | 20.4/>100 | 22.6/>100 | 0.41/52.4 |
| Prostate Cancer* | 16.6 | 21.2 | 33.6 | 3.13 |
| PC-3 | 13.2/>100 | 13.7/>100 | 30.9/>100 | 2.78/>100 |
| DU-145 | 20.1/>100 | 28.6/>100 | 36.3/>100 | 3.48/>100 |
| Breast Cancer* | 10.0 | 14.3 | 33.3 | 2.00 |
| NCI/ADR-RES | 10.4/>100 | 16.5/71.0 | 15.9/>100 | 0.37/>100 |
| MDA-MB-435 | 3.23/>100 | 3.52/>100 | 5.30/>100 | 0.11/>100 |

*The $IC_{50}$ value was the average value of all the cancer cell lines involved in the various kinds of human cancer cells.
$^a$The concentration produced 50% reduction in cell growth.
$^b$The concentration produced 50% cells killed.

TABLE 5

The in vitro anticancer activities of compound 40.

| | $GI_{50}/LC_{50}$ |
|---|---|
| Leukmia* | 12.3/64.8 |
| HL-60 (TB) | 9.32/50.9 |
| K-562 | 2.12/68.3 |
| MOLT-4 | <0.01/18.3 |
| Non-Small cell Lung cancer* | 28.6/>100 |
| NCI-H23 | 18.6/93.5 |
| NCI-H460 | 15.7/>100 |
| NCI-H522 | 15.4/93.9 |
| Colon cancer* | 39.0/>100 |
| HCT-15 | 17.8/>100 |
| KM12 | 29.7/>100 |
| CNS cancer* | 48.6/>100 |
| SF-268 | 19.7/>100 |
| SF-295 | 25.3/>100 |
| Melanoma* | 23.9/94.8 |
| LOX IMVI | 15.9/>100 |
| SK-MEL-2 | 15.1/91.8 |
| SK-MEL-5 | 16.9/76.6 |
| UACC-257 | 13.3/88.7 |
| Ovarian Cancer* | 20.2/>100 |
| IGROV1 | 5.23/70.6 |
| OVCAR-3 | 16.2/98.4 |
| OVCAR-8 | 22.0/>100 |
| Renal cancer* | 23.1/>100 |
| ACHN | 16.7/>100 |
| CAKI-1 | 12.7/>100 |
| UO-31 | 16.3/>100 |
| Prostate cancer* | 29.9/>100 |
| PC-3 | 28.7/>100 |
| Breast cancer* | 27.2/>100 |
| MCF7 | 18.2/>100 |
| NCI/ADR-RES | 19.9/>100 |
| MDA-MB-435/ATCC | 27.5/>100 |
| MDA-MB-435 | 16.2/>100 |

TABLE 6

The in vitro anticancer activities of compounds 34, 37, 38 and 41.

| | 34 | | 37 | | 38 | | 41 | |
|---|---|---|---|---|---|---|---|---|
| | $GI_{50}$ | $LC_{50}$ | $GI_{50}$ | $LC_{50}$ | $GI_{50}$ | $LC_{50}$ | $GI_{50}$ | $LC_{50}$ |
| Leukmia* | 2.43/>100 | | 2.45/>100 | | 7.05/87.6 | | 29.3/>100 | |
| MOLT-4 | 1.04/>100 | | 2.12/>100 | | 3.44/66.8 | | 25.8/>100 | |
| K-562 | 0.58/>100 | | 2.01/>100 | | 7.02/92.2 | | 30.2/>100 | |
| Non-Small cell Lung cancer* | 16.9/>100 | | 10.8/82.7 | | 17.5/85.1 | | 63.4/>100 | |
| HOP-62 | 1.20/>100 | | 3.62/52.4 | | 1.92/50.0 | | 77.3/>100 | |
| NCI-H460 | 6.51/>100 | | 5.89/>100 | | 23.1/>100 | | 47.4/>100 | |
| NCI-H522 | 16.3/>100 | | 3.17/55.7 | | 16.3/81.0 | | 34.2/>100 | |
| Colon cancer* | 12.5/85.1 | | 7.57/82.1 | | 17.4/80.9 | | 28.2/>100 | |
| HCC-2998 | 0.03/65.2 | | 14.0/>100 | | 4.77/62.8 | | 24.0/>100 | |
| KM12 | 3.26/>100 | | 2.97/>100 | | 11.0/47.9 | | 29.5/>100 | |
| SW-620 | 2.91/93.3 | | 5.32/66.4 | | 21.2/>100 | | 42.0/>100 | |
| CNS cancer* | 20.1/86.2 | | 11.7/76.1 | | 17.3/75.6 | | 78.2/>100 | |
| SF-295 | 7.71/71.9 | | 3.13/49.3 | | 16.8/66.1 | | 30.6/>100 | |
| U251 | 13.9/74.8 | | 4.50/47.0 | | 11.5/55.7 | | 66.8/>100 | |
| Melanoma* | 16.3/82.2 | | 12.1/71.0 | | 17.6/72.4 | | 52.8/>100 | |
| M14 | 5.04/80.1 | | 6.62/74.2 | | 22.1/>100 | | 32.9/>100 | |
| SK-MEL-5 | 1.95/47.6 | | 9.09/55.0 | | 15.5/61.9 | | 23.5/>100 | |
| MALME-3M | 7.86/>100 | | 10.3/56.2 | | 7.75/47.0 | | 56.9/>100 | |
| Ovarian Cancer* | 22.1/92.7 | | 16.5/88.1 | | 22.4/89.7 | | 66.7/>100 | |
| OVCAR-3 | 1.72/55.9 | | 2.22/54.3 | | none | | 57.1/>100 | |
| Renal cancer* | 14.1/>100 | | 8.56/70.1 | | 14.9/74.7 | | 36.5/>100 | |
| CAKI-1 | 6.86/>100 | | 4.41/71.7 | | 18.3/98.9 | | 43.2/>100 | |
| TK-10 | 8.33/>100 | | 4.17/72.9 | | 6.54/60.3 | | 27.6/>100 | |
| Prostate cancer* | 17.1/97.0 | | 8.31/69.9 | | 16.7/70.1 | | 62.7/>100 | |
| PC-3 | 7.31/94.3 | | 5.31/67.7 | | 13.5/67.1 | | 25.4/>100 | |
| Breast cancer* | 9.98/>100 | | 9.71/75.9 | | 14.6/86.9 | | 43.2/>100 | |

TABLE 6-continued

The in vitro anticancer activities of compounds 34, 37, 38 and 41.

| | 34 $GI_{50}$ | $LC_{50}$ | 37 $GI_{50}$ | $LC_{50}$ | 38 $GI_{50}$ | $LC_{50}$ | 41 $GI_{50}$ | $LC_{50}$ |
|---|---|---|---|---|---|---|---|---|
| MDA-MB-435 | 1.43/64.6 | | 1.31/26.4 | | 8.43/54.4 | | 37.2/>100 | |
| NCI/ADR-RES | 2.26/>100 | | 13.0/>100 | | 5.45/>100 | | 25.2/>100 | |

According to the cytotoxicities observed in the NCI screening data, the compounds of this invention displayed good activities in growth inhibition of ten usual human cancers, including leukemia, non-small cell lung cancer, colon cancer, CNS cancer, melanoma, ovarian cancer, renal cancer, prostate cancer, breast cancer and liver cancer. The $IC_{50}$ values of several of the compounds were $10^{-7}$ M or $10^{-8}$ M, and the acute toxicities ($LC_{50}$ values) of most active compounds were larger than $10^{-4}$ M (data collected by NCI).

B. Evaluation of Inhibitory Concentration of Camptothecin for Gel Electrophoresis.

Camptothecin, which showed significant topo I inhibition, was widely used as the standard for the comparison of activity to the novel compounds. Regarding the modest concentration of camptothecin that would exhibit explicit suppression of topo I and used in the following experimental section as comparison, various concentrations were prepared, and the results were obtained by agarose gel electrophresis. It was suggested that camptothecin showed less topo I inhibitory activity when the concentration was 26.1 µM. On the other hand, 43.5 µM of camptothecin exhibited observable inhibition of topo I. Therefore, the 43.5 µM was used as the standard concentration of camptothecin, when the inhibition of topo I was proceeded (data not shown).

Figure 2:
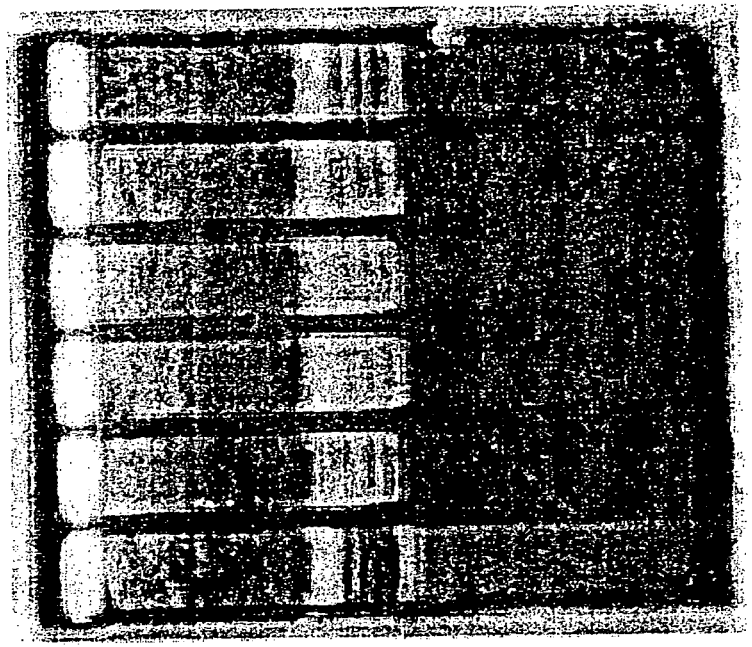
FIG. 2 shows the cleavage of supercoiled pGEM9zf(-) DNA by topoisomerase I in the presence of 1-aryl-3-decen-1,5-diynes 13-23, in which in panel (a), lane 1: DNA only; lane 2: DNA+topo I; lanes 3-7: DNA+topo I+compounds 13-17 (87 µM); and in panel (b), lanes 1-6: DNA +topo I+compounds 18-23 (87 µM).
Figure 2:
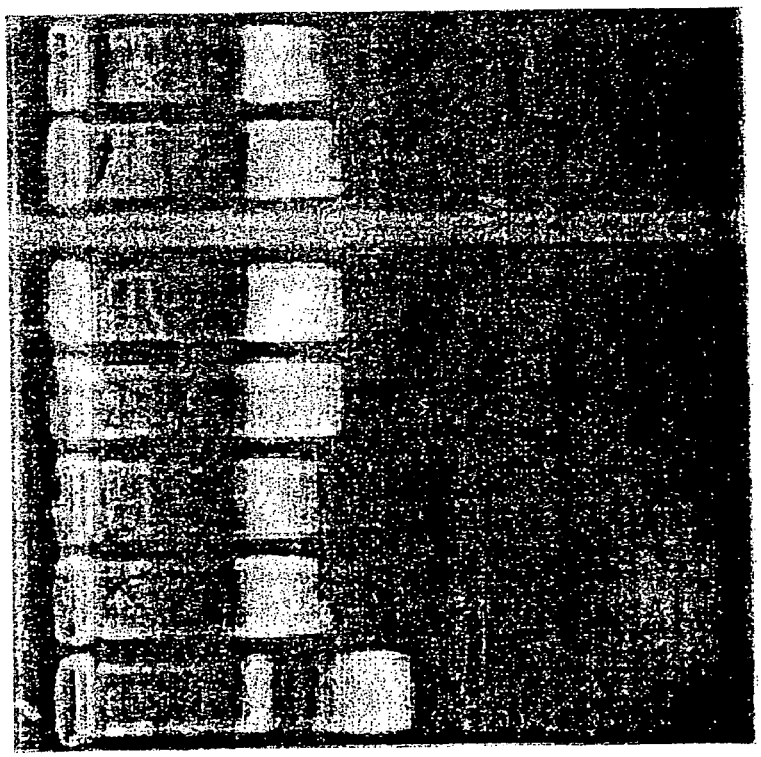

C. Inhibition Tests of the Compounds 7-23 for Topoisomerase I:

The cleavage of supercoiled DNA by topo I in the presence of 2-(2-(2-alkynylphenyl)ethynyl)benzonitriles 7-10, 1,4-bis(3-decen-1,5-diynyl) benzene 11, 4,4'-bis(3-decen-1,5-diynyl)biphenyl 12, and 1-aryl-3-decen-1,5-diynes 13-23 were evaluated by gel electrophoresis, and the results are shown in FIGS. 1 and 2.

Supercoiled pGEM9zf(-) DNA was treated with 0.025 µg/µl topoisomerase I and compounds 7-10 and compounds 11-12 (the unshown results of compounds 7 and 8 display no Topo I inhibition at 8.7 and 87 µM), then analyzed on a 2% agarose gel. In panel (a), lane 1: DNA+topo I; lane 2: DNA only; lane 3: DNA+topo I+camptothecin (43.5 µM); lanes 4-6. DNA+topo I+compound 10; lanes 7-9: DNA+topo I+compound 9. Each group of three lanes contained 0.87, 8.7, 87 µM of the analogs, respectively. In panel (b), lane 1: DNA+topo I; lane 2: DNA only; lanes 3-4: DNA+topo I+compound 11; and lanes 5-6: DNA+topo I+compound 12. Each group of both lanes contained 8.7, 87 µM of the analogs, respectively.

In panel (a) of FIG. 1, compound 10 displayed inhibitory activity against topo I at 8.7, 87 µM, and no inhibition of topo I at 0.87 µM concentration. Compound 9 showed restraint of topo I at 87 µM, and there was no supercoiled DNA observed at 8.7 or 0.87 µM. Moreover, untwisting DNA was revealed at 0.87, 8.7 and 87 µM of compound 7 and compound 8 (data not shown). No supercoiled DNA was observed for bis-enediynes 11 and 12 at 8.7 or 87 µM concentration (panel (b) of FIG. 1).

Supercoiled pGEM9zf(-) DNA was treated with 0.025 µg/µl topoisomerase I and compounds 13-23, and then analyzed on a 2% agarose gel. In panel (a), lane 1: DNA only; lane 2: DNA+topo I; and lanes 3-7: DNA+topo I+compounds 13-17 (87 µM). In panel (b), lanes 1-6: DNA+topo I+compounds 18-23 (87 µM).

In panel (a) of FIG. 2, 1-aryl-3-dodecen-1,5-diynes 13-17 exhibited no inhibition effects with topo I. 4-(3-(Z)-dodecen-1,5-diynyl)trifluoromethyl-benzene 18 and 4-(3-(Z)-Dodecen-1,5-diynyl)acetophenone 23 displayed inhibitory activities of topo I on the test concentration in panel (b) of FIG. 2.

D. Cell Cycle Assay:

To obtain more information about the effect(s) of the acyclic enediynes according to this invention upon the growth of cells, human hepatoma Hep G2 cells or K-562 cells were used, and the growth characteristic of said cells were measured subsequent to the treatment with a test compound.

Figure 3:
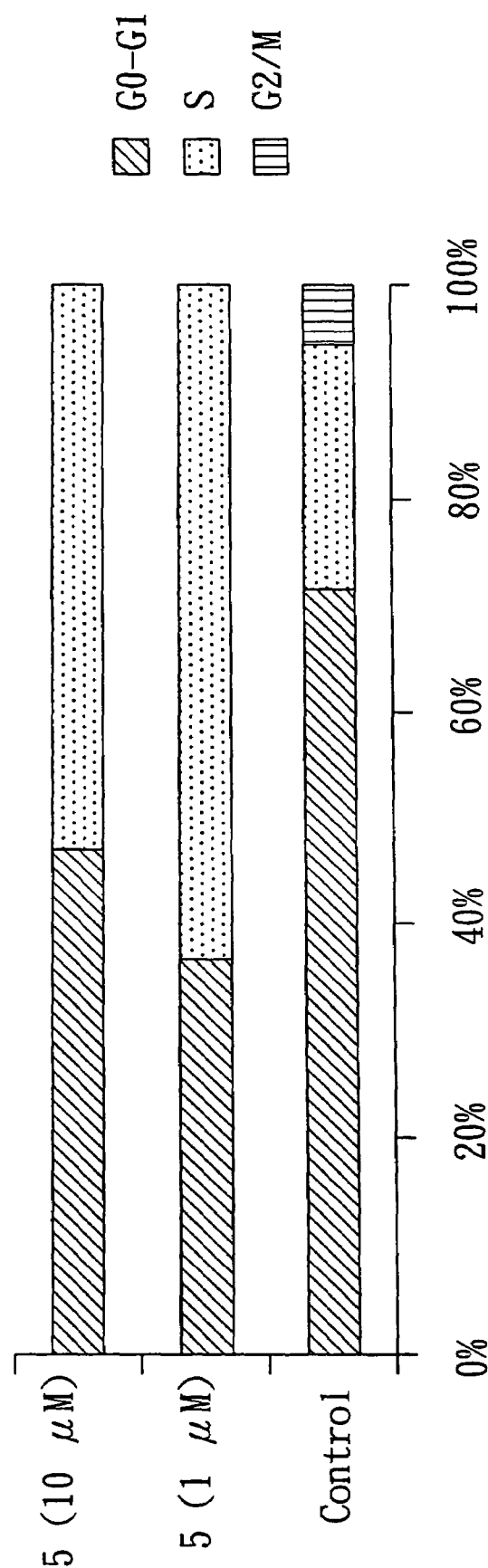
FIG. 3 shows the effect of compound 5 according to this invention on cell-cycle distribution [%] of human hepatoma Hep G2 cells for 72 hrs. Cell-cycle distribution of human hepatoma Hep G2 cells were measured by flow cytometry. Values are expressed as mean for triplicate samples (significantly different from control, p<0.05)

As shown in FIG. 3, cells were exposed to the vehicle solvent (DMSO) as control. 1 µM or 10 µM of compound 5 was added to the cells, and after exposure to the compounds for 72 hrs, attached cells were analyzed by flow cytometry. The majority (71.5%) of control cells exposed to DMSO were in the G0-G1 phase of cell cycle, and only a small amount of cells was detected in either the S phase (22.7%) or G2/M (5.8%) phase. Moreover, after a 72 hrs treatment with compound 5 (1 and 10 µM), cells progressed to the S phase and the majority of cell population was almost arrested at the S phase. Consistent with this cell cycle arrest, only 36.6% (1 µM) and 46.9% (10 µM) of the cells were found at the G0-G1 phase, 63.2% (1 µM) and 53.0% (10 µM) in S phase, and 0.2% (1 µM) and 0.1% (10 µM) in G2/M phase. However, the significant blockage of the Hep G2 cell cycle in S phase was observed and was induced by both concentrations (1 µM and 10 µM) of compound 5.

There are two essential factors that may facilitate the enediyne derivatives against topo I, i.e. the enediyne core and the cyano group substituted on the o-position of benzene. The enediynes 2-5 reveal inhibition of topo I (C. F. Lin, P. C. Hsieh, W. D. Lu, H. F. Chiu, M. J. Wu, *J. Bioorg. Med. Chem.* 2001, 9, 1707). Replacement of the enediyne core with 1,2-diethynyl benzene lowers the inhibition abilities of topo I, which may be due to the alteration of conformation of the original enediyne core, or because of the lowered ability of 1,2-diethynyl benzene to form a complex with topo I as compared with the original enediyne core.

All unwinding DNAs detected in panel (b) of FIG. 1 indicate that compounds 11 and 12 are not topo I inhibitors. The results clearly show that increasing the quantities of enediyne core cannot enhance the activity against topo I. Further, it is observed that only compounds 18 and 23 displayed topo I inhibitory activities amongst 1-aryl-3-dodecen-1,5-diynes 13-23. Hence, it is considered that topoisomerase I inhibitors have high structural selectivity. The observed phenomenon that compound 6 and it's dimer 12 are not Topo I inhibitors but show activities against KB cell suggests the structure of compounds 12 and 6 might interfere with an unknown biological path to cause the cytotoxic activity.

In view of the above, the acyclic enediynes according to this invention displayed selective inhibitory effects upon the growth of a variety of human tumor cells, and some of them revealed inhibitory effects with topoisomerase I, although there seems to be no significant relationship between the cytotoxicity and topo I.

On the other hand, it was considered that the intact cancer cells owned complete biological functions. Hence, it is possible that other compensatory pathways in the cancer cells would be active when topoisomerase I was inhibited during the periods of DNA replication. The data shown in bounded to theory, a hypothesis for the structural relationships of the biological activities of three series of nonradical enediynes is proposed in the following scheme 6.

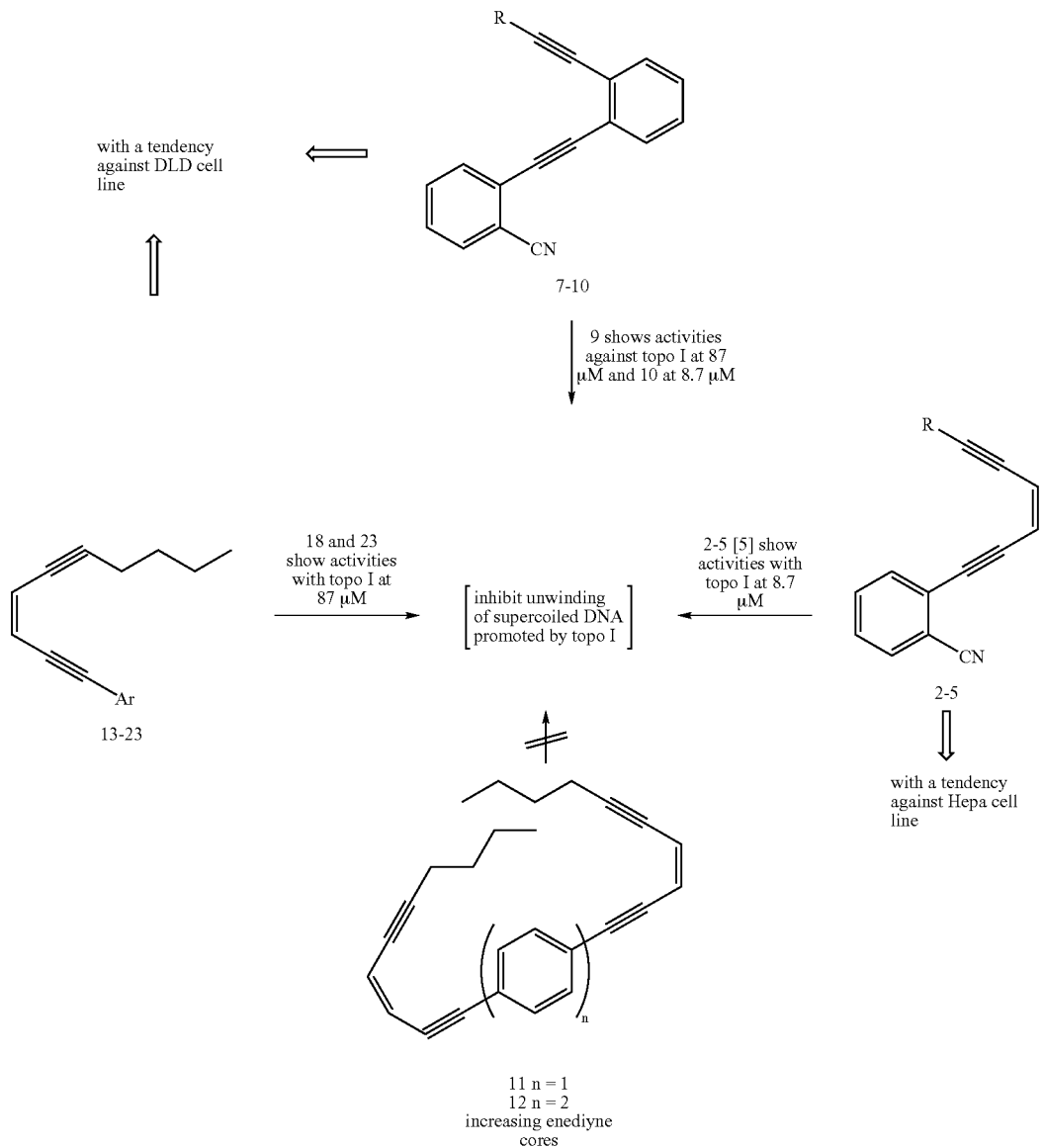

FIG. 3 demonstrated that compound 5 induced a blockage of cell growth cycle in S phase. It was thought that only inhibiting topoisomerase I could not completely arrest the cell cycle in the S phase. Therefore, the results of FIG. 3 suggested that compound 5 not only targeted the topo I, but also interfered with the topo II. Moreover, in general, the cells progressed to a final accrual at G2/M or later phase. The observed small amount of G2/M cells also implied that compound 5 probably inhibited the mitosis or tubulin polymerization, though more evidence is needed to support this conclusion. However, the significant blockage of the Hep G2 cell cycle in S phase suggested that the enediynes according to this invention probably underwent other biological pathways to give the cytotoxicity. While not wishing not to be Although the picture concerning the cytotoxicities of the compounds according to this invention is still incomplete, we discovered that several new lead compounds of enediynes provided potent activities against a variety of human solid tumor cells and topo I, and the cell cycle test of compound 5 indicates that the enediyne structures block the replication of DNA.

Figure 4:
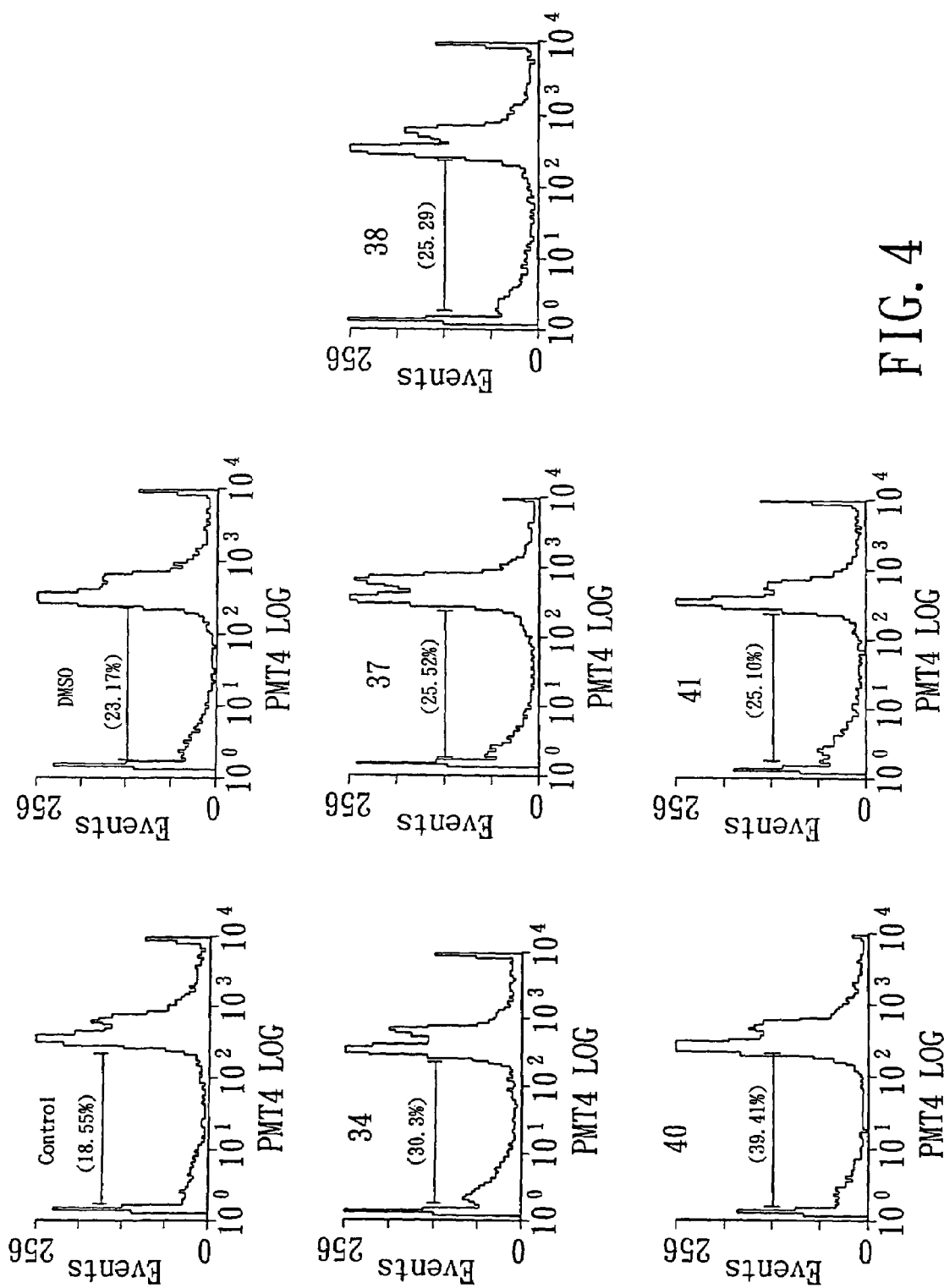
FIG. 4 shows the effects of compound 34, 37, 38, 40 and 41 according to this invention upon cell cycle distribution of K-562 cells as assessed by flow cytometry analysis.
Figure 5:
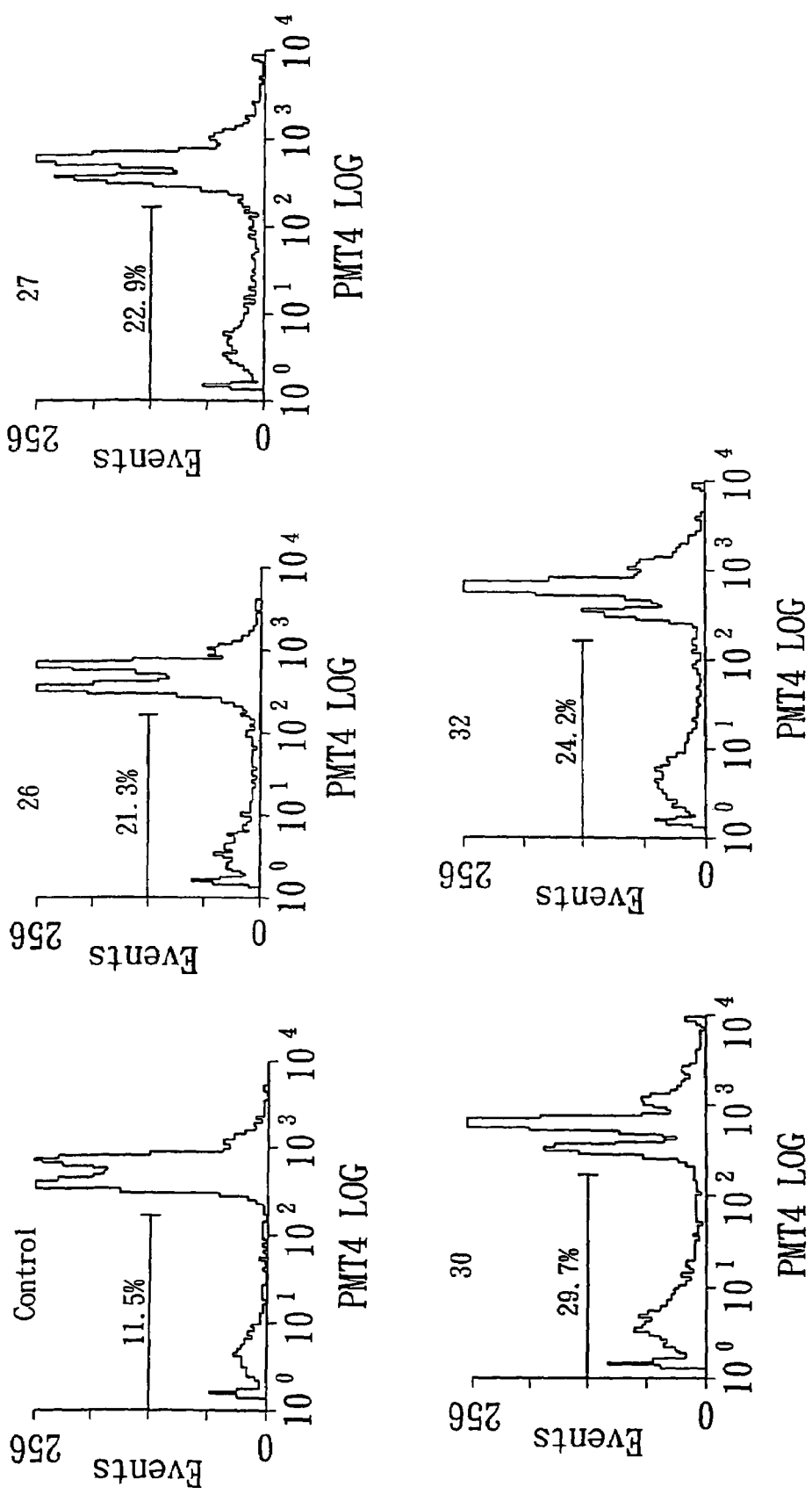
FIG. 5 shows the effects of compounds 26, 27, 30 and 32 according to this invention upon the cell cycle distribution of K-562 cells as assessed by flow cytometry analysis.
Figure 6:
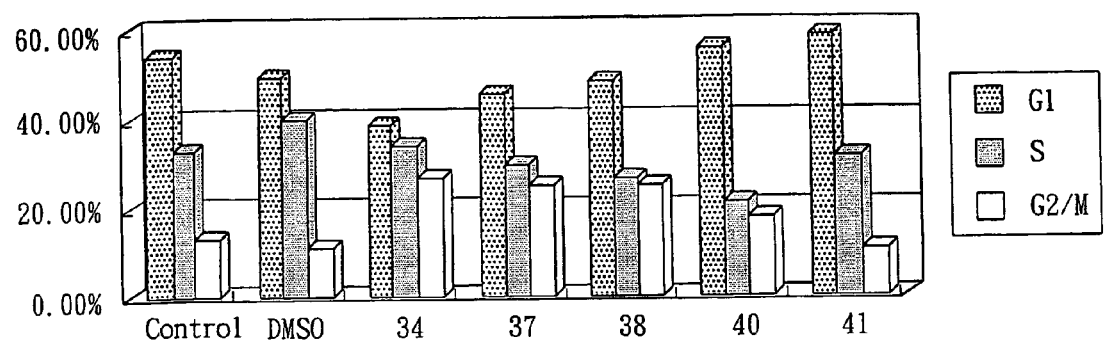
FIG. 6 shows the cell cycle distribution of K-562 cells after being treated with compounds 34, 37, 38, 40 and 41 according to this invention and control.
Figure 7:
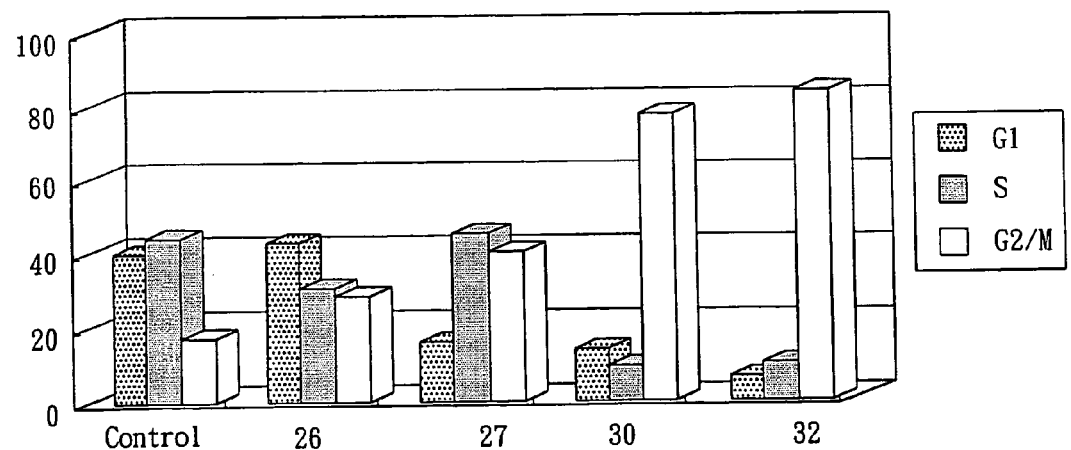
FIG. 7 shows the cell cycle distribution of K-562 cells after being treated with compounds 34-43 according to this invention and DMSO.
Figure 8:
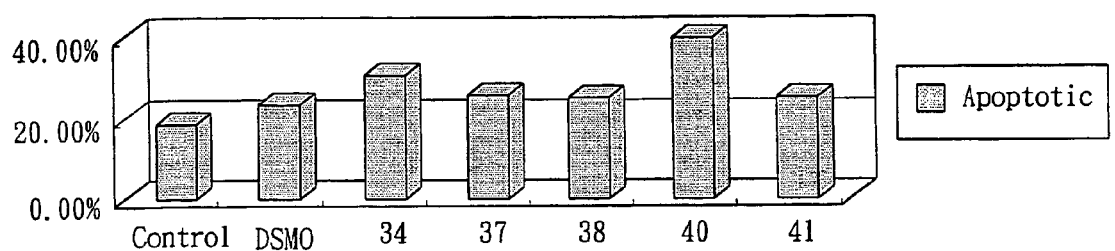
FIG. 8 shows the apoptotic effects induced by compounds 34, 37, 38, 40 and 41 according to this invention and control.
Figure 9:
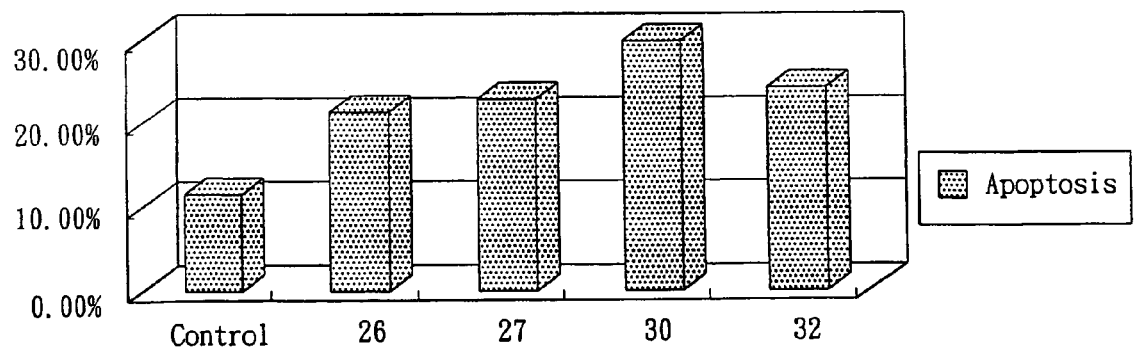
FIG. 9 shows the apoptotic effects induced by compounds 26, 27, 30 and 32 according to this invention and control.

Referring to FIGS. 4 and 5, when K-562 cells were treated with compounds 26, 27, 30, 32, 34, 37, 38, 40 and 41 for 72 hrs, an accumulation of G2/M stage cells in these samples is observed. In addition, as shown in FIGS. 6 and 7, the percentage of cells at the G2/M phase increased from 17% to 84% after treatment of K-562 cells with compounds 26, 27, 30, 32, 34, 37, 38, 40 and 41, respectively. Further, the nine compounds caused the formation of apoptotic K-562 cells at 50 FM, and the proportion of apoptotic cells varied from 21.3% to 40.0% (FIGS. 8 and 9).

In general, there are two types of cellular death: necrosis and apoptosis. Necrotic cells were killed by external or tumor necrotic factors (TNF), while apoptotic cells participated in their own destruction. The presentation of apoptotic effect excluded the TNF for providing cytotoxicities to cancer cells in the presence of compounds 24-43. Usually, the apoptotic process was very complex. An important part of this phenomenon could be mediated by deregulation in cell cycle progression governed by a family of cyclin-dependent kinases (CDKs), although much more experimental evidence is necessary to support this hypothesis. It is found in this invention that 3,4-disubstituted-1,6-diaryl-3-hexen-1,5-diynes 24-43 may act as G2/M phase blocker. Investigation of the actual mechanism of acyclic 1,6-diaryl-3-hexen-1,5-diynes 24-43 in inhibiting the growth of tumor/cancer cells is still ongoing.

In this invention, we provided new 6-aryl-3-hexen-1,5-diynes of formula (I), which are found for the first time to have inhibitory activities against a variety of human tumor cells at low concentration (the highest $IC_{50}$ value is 0.1 μM or 1 μg/ml), and whose activities do not arise from the formation of biradical intermediates as usually known. The main drawback of the existing anticancer drugs commonly used in clinical therapies is the occurrence of serious side effects subsequent to the administration of the drugs, which may undesirably result in the death of normal cells. Most of the $LC_{50}$ values of these compounds are higher than 100 μM, which means that these compounds display the growth inhibition of human tumor cell lines and cause almost no normal cell death (caused lower side-effect). It is an important advancement for cancer therapies.

On the other hand, rigmarole synthetic procedures are frequent problems for most antitumor drugs. However, the acyclic 6-aryl-3-hexen-1,5-diynes of formula (I) according to this invention are easy to prepare. Moreover, by modification of the active structures, active anticancer or antivirus compounds with less side effects could be conveniently developed in the future.

All literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:
1. A compound of formula (I):

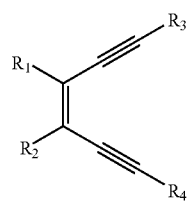

(I)

or a pharmaceutically acceptable salt thereof, wherein
$R_1=R_2=H$; or $R_1$ and $R_2$ together form a moiety represented by the formula

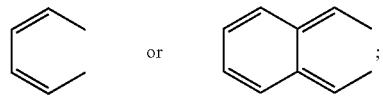

$R_3$ represents a substituted alkyl having 4-30 carbon atoms, wherein the alkyl group is substituted with one to three substituents selected from the group consisting of halo, cyano, amino, nitro, carbonyl, carboxyl, hydroxy, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, and $C_1$-$C_6$ alkanoyloxy,
a substituted aryl group having 3-30 carbon atoms, wherein the aryl group is substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy, t-butyldimethylsilyloxy, and phenyl
tetrahydropyranyloxyalkyl, or
($C_5$-$C_8$ aryl)oxyalkyl; and
$R_4$ represents
(A) a substituted or unsubstituted aryl group having 3-30 carbon atoms, wherein the aryl group is optionally substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy, t-butyldimethylsilyloxy, and phenyl; or
(B) ($C_5$-$C_8$ aryl)oxyalkyl, tetrahydropyranyloxyalkyl;
(C) a substituted phenylene or biphenylene group represented as

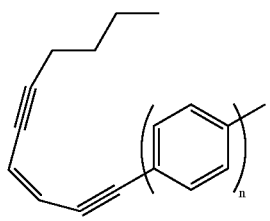

where n is 1 or 2.

2. The compound of claim 1, wherein both $R_1$ and $R_2$ are H.

3. The compound of claim 1, wherein $R_1$ and $R_2$ together form a moiety represented by the formula

4. The compound of claim 1, wherein
$R_3$ represents a substituted alkyl having 4-20 carbon atoms, or a substituted aryl group having 3-20 carbon atoms; and
$R_4$ represents a substituted or unsubstituted aryl group having 3-20 carbon atoms.

5. The compound of claim 1, wherein $R_3$ represents:

pentyl, hexyl, heptyl or octyl, each of which is substituted with one to three substituents selected from the group consisting of halo, cyano, amino, nitro, carbonyl, carboxyl, hydroxy, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, and $C_1$-$C_6$ alkanoyloxy;

thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl;

($C_5$-$C_8$ aryl)oxyalkyl; or a phenyl group which is substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1C_6$ alkanoyl, $C_1$-$C_6$ alkanoyloxy and t-butyldimethylsilyloxy.

6. The compound of claim 5, wherein $R_3$ represents:

tetrahydropyranyloxyalkyl, 5-methylthienyl, 2-uracilyl, 2,4-dimethylpyrimidinyl, 1-(4-phenyl)pyrrolyl, 1-(4-phenyl)pyrrolidinyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl or 2-thioanisyl.

7. The compound of claim 6, wherein $R_3$ is an aryl group selected from o-cyanophenyl, m-cyanophenyl, p-cyanophenyl, p-trifluoromethylphenyl, m-trifluoromethylphenyl, o-trifluoromethylphenyl,

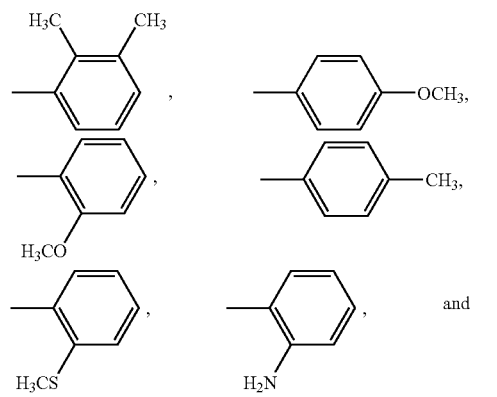

and

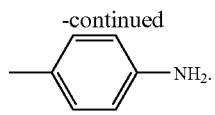

8. The compound of claim 1, wherein $R_4$ represents:

thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is optionally substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl;

($C_5$-$C_8$ aryl)oxyalkyl; or a phenyl group which is unsubstituted or substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

9. The compound of claim 8, wherein $_4$ represents:

2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, 1-(4-phenyl)pyrrolidinyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl, or 2-thioanisyl.

10. The compound of claim 9, wherein $R_4$ is an aryl group selected from:

o-cyanophenyl, m-cyanophenyl, p-cyanophenyl, p-trifluoromethylphenyl, m-trifluoromethylphenyl, o-trifluoromethylphenyl,

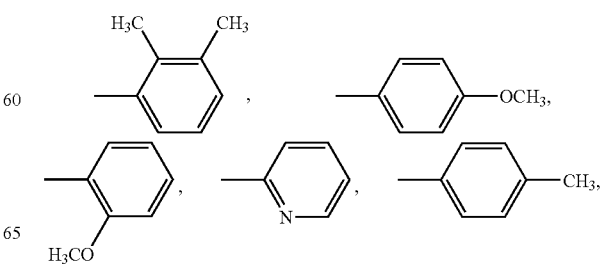

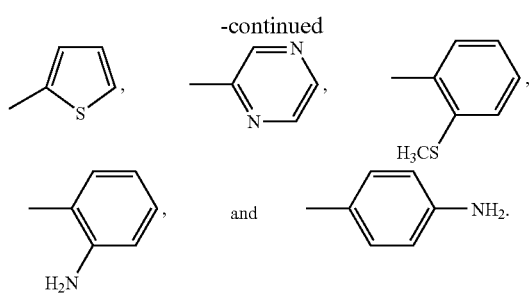

11. The compound of claim 1, wherein the compound of formula (I) is one having the following formula (IA);

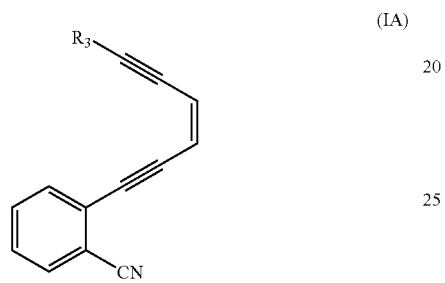

(IA)

or a pharmaceutically acceptable salt thereof, wherein $R_3$ represents:

a tetrahydropyranyloxyalkyl group excluding tetrahydropyranyloxymethyl and tetrahydropyranyloxypropyl;

thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl; or a phenyl group which is substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

12. The compound of claim 11, wherein $R_3$ is an aryl group selected from 5-methylthienyl, 2-uracilyl, 2,4-dimethylpyrimidinyl, 1-(4-phenyl)pyrrolyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl, and 2-thioanisyl.

13. The compound of claim 11, wherein $R_3$ is an aryl group selected from o-cyanophenyl, m-cyanophenyl, p-cyanophenyl, p-trifluoromethylphenyl, m-trifluoromethylphenyl, o-trifluoromethylphenyl,

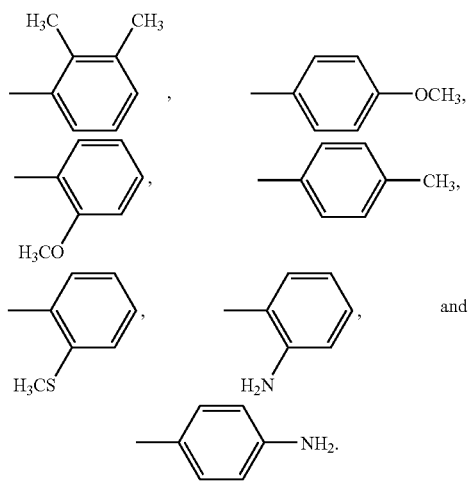

14. The compound of claim 1, wherein the compound of formula (I) is one having the following formula (IB):

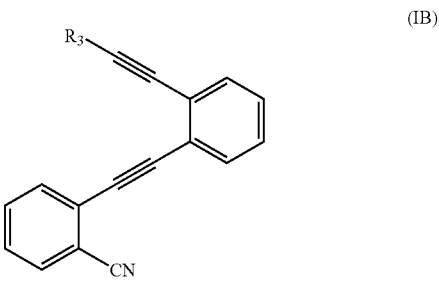

(IB)

or a pharmaceutically acceptable salt thereof, wherein $R_3$ represents:

pentyl, hexyl, heptyl or octyl, each of which is substituted with one to three substituents selected from the group consisting of halo, cyano, amino, nitro, carbonyl, carboxyl, hydroxy, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, and $C_1$-$C_6$ alkanoyloxy;

thienyl, pyridinyl, piperidyl, pyrazinyl, cyclohexenyl, triisopropylsilyl, pyrrolyl, pyrrolinyl, pyridazinyl, pyrimidinyl, furanyl, uracilyl or pyrazolyl, each of which is substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl;

($C_5$-$C_8$ aryl)oxyalkyl; or a phenyl group which is substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

15. The compound of claim 14, wherein $R_3$ represents: tetrahydropyranyloxyalkyl, 5-methylthienyl, 2-uracilyl, 2,4-dimethylpyrimidinyl, 1-(4-phenyl)pyrrolyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl or 2-thioanisyl.

16. The compound of claim 14, wherein $R_3$ is tetrahydropyranyloxymethyl or tetrahydropyranyloxypropyl, or an aryl group selected from o-cyanophenyl, m-cyanophenyl, p-cyanophenyl, p-trifluoromethylphenyl, m-trifluoromethylphenyl, o-trifluoromethylphenyl,

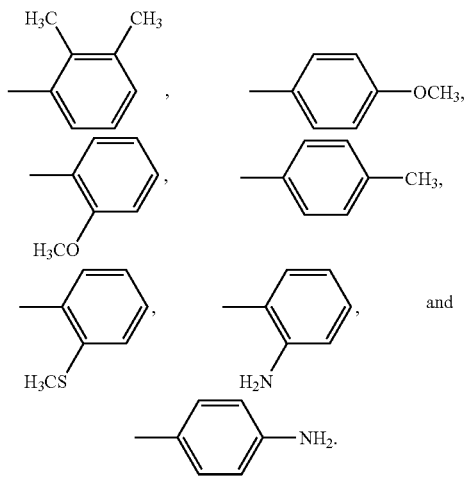

17. A compound having the following formula (IC):

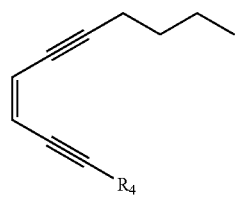

(IC)

or a pharmaceutically acceptable salt thereof, wherein $R_4$ represents:
thienyl, pyridinyl, piperidyl, pyrazinyl, cyclohexenyl, triisopropylsilyl, pyrrolyl, pyrrolinyl, pyridazinyl, pyrimidinyl, furanyl, uracilyl or pyrazolyl, each of which is optionally substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and phenyl;

($C_5$-$C_8$ aryl)oxyalkyl;

tetrahydropyranyloxyalkyl; or a phenyl group which is substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$ hydroxyalkyl, $C_1$-$C_6$ haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

18. The compound of claim 17, wherein $R_4$ represents: tetrahydropyranyloxyalkyl, 2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl, or 2-thioanisyl.

19. The compound of claim 18, wherein $R_4$ is an aryl group selected from:
m-cyanophenyl, p-cyanophenyl, p-trifluoromethylphenyl, m-trifluoromethylphenyl, o-trifluoromethylphenyl,

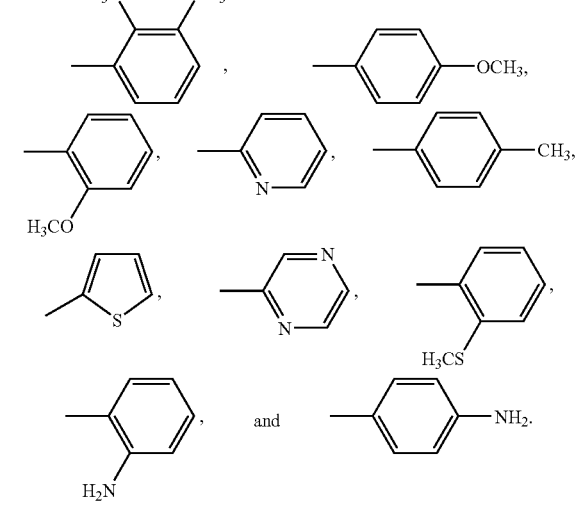

20. A compound having the formula

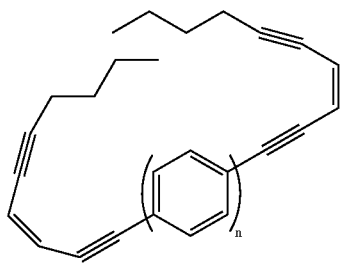

where n is 1 or 2.

21. The compound of claim 1, wherein the compound of formula (I) is one having the following formula (ID):

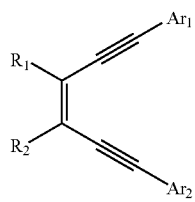

(ID)

or a pharmaceutically acceptable salt thereof, wherein $Ar_1$ and $Ar_2$ independently represent a group selected from thienyl, pyridinyl, piperidyl, pyrazinyl, cyclohexenyl, triisopropylsilyl, pyrrolyl, pyrrolidinyl, pyrrolinyl, pyridazinyl, pyrimidinyl, furanyl, uracilyl or pyrazolyl, each of which is substituted with one to three substituents selected from the group consisting of halo, cyano, amino, nitro, carbonyl, carboxyl, hydroxy, $C_1$-$C_6$ hydroxyalkyl, $C_1$-$C_6$ alkyl, $C_1$-$C_6$haloalkyl, $C_1$-$C_6$ alkoxy, $C_1$-$C_6$ alkylthio, $C_1$-$C_6$ alkanoyl, $C_1$-$C_6$ alkanoyloxy and phenyl;

tetrahydropyranyloxyalkyl;

($C_5$-$C_8$ aryl)oxyalkyl; or a phenyl group which is substituted with one to three substituents selected from the group consisting of halo, cyano, amino, nitro, carbonyl, carboxyl, hydroxy, hydroxycarbonyl, $C_1$-$C_6$ alkyl, $C_1$-$C_6$hydroxyalkyl, $C_1$-$C_6$haloalkyl, $C_1$-$C_6$ alkoxy, $C_1$-$C_6$ alkylthio, $C_1$-$C_6$ alkanoyl, $C_1$-$C_6$ alkanoyloxy and t-butyldimethylsilyloxy.

22. The compound of claim 21, wherein $Ar_1$ and $Ar_2$ independently represent: tetrahydropyranyloxyalkyl, 2-thienyl, 3-thienyl, 5-methylthienyl, 2-pyridinyl, 3-pyridinyl, 4-pyridinyl, 2-pyrazinyl, pyrazinyl, pyrazolyl, 3-pyridazinyl, 2-furanyl, 3-furanyl, 2-uracilyl, 2,4-dimethylpyrimidinyl, 1-(4-phenyl)pyrrolyl, o-cyanophenyl, m-cyanophenyl, p-cyanophenyl, o-cyanomethylphenyl, m-cyanomethylphenyl, p-cyanomethylphenyl, p-chlorophenyl, 2-acetylphenyl, 2-nitrophenyl, 3-nitrophenyl, 4-nitrophenyl, 2-hydroxyphenyl, 3-hydroxyphenyl, 4-hydroxyphenyl, 2-methylphenyl, 3-methylphenyl, 4-methylphenyl, 2-formylphenyl, 3-formylphenyl, 4-formylphenyl, 2-methoxyphenyl, 3-methoxyphenyl, 4-methoxyphenyl, 2-anilinyl, 4-anilinyl, 3-aminomethylphenyl, 2-chloromethylphenyl, 1,3,5-trichlorophenyl, 2-hydroxycarbonylphenyl, 3-hydroxycarbonylphenyl, 4-hydroxycarbonylphenyl, 2-methylhydroxylphenyl, 3-methylhydroxylphenyl, 4-methylhydroxylphenyl, p-trifluoromethylphenyl, m-trifluoromethylphenyl, o-trifluoromethylphenyl, 2,3-dimethylphenyl or 2-thioanisyl.

23. The compound of claim 21, wherein $Ar_1$ and $Ar_2$ independently represent an aryl group selected from o-cyanophenyl, m-cyanophenyl, p-cyanophenyl, p-trifluoromethylphenyl, m-trifluoromethylphenyl, o-trifluoromethylphenyl,

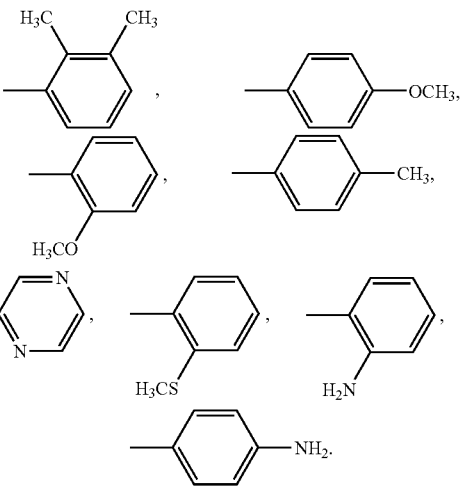

24. The compound of claim 21, wherein $Ar_1$ and $Ar_2$ are identical and represent an aryl group selected from o-cyanophenyl, m-cyanophenyl, p-cyanophenyl, p-trifluoromethylphenyl, m-trifluoromethylphenyl, o-trifluoromethylphenyl,

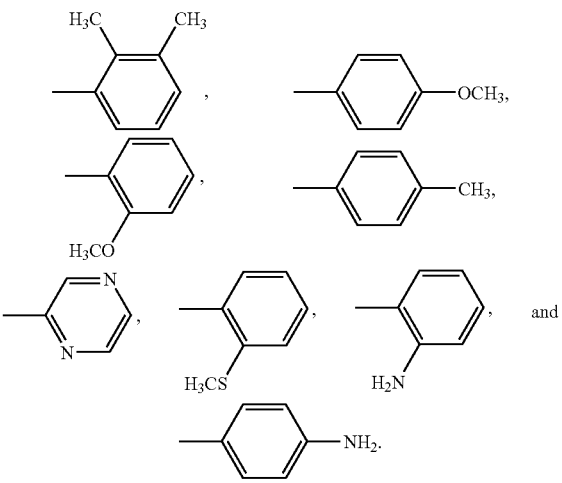

* * * * *